(12) United States Patent
Lim et al.

(10) Patent No.: US 7,309,793 B2
(45) Date of Patent: Dec. 18, 2007

(54) BENZOPYRAN DERIVATIVES SUBSTITUTED WITH A BENZIMIDAZOLE DERIVATIVE, PHARMACEUTICALLY ACCEPTABLE SALTS THEROF, THEIR PREPARATIONS AND PHARMACEUTICAL COMPOSITIONS CONTAINING THEM

(75) Inventors: Hong Lim, Seoul (KR); Dong Ha Lee, Taejon-si (KR); Sun Ok Kim, Taejon-si (KR); Sung-Eun Yoo, Kongju-si (KR); Kyu Yang Yi, Taejon-si (KR); Sun Kyung Lee, Taejon-si (KR); Jee Hee Suh, Taejon-si (KR); Nak Jeong Kim, Taejon-si (KR); Sun Kyung Hwang, Taejon-si (KR); Tae Mi Kim, Taejon-si (KR); Byung Ho Lee, Taejon-si (KR); Ho-Won Seo, Taejon-si (KR)

(73) Assignee: Dongbu Hannong Chemical Co., Ltd., Seoul (KR)

( * ) Notice: Subject to any disclaimer, the term of this patent is extended or adjusted under 35 U.S.C. 154(b) by 30 days.

(21) Appl. No.: 10/558,020

(22) PCT Filed: May 28, 2004

(86) PCT No.: PCT/KR2004/001269

§ 371 (c)(1),
(2), (4) Date: Nov. 23, 2005

(87) PCT Pub. No.: WO2004/106330

PCT Pub. Date: Dec. 9, 2004

(65) Prior Publication Data

US 2006/0293376 A1    Dec. 28, 2006

(30) Foreign Application Priority Data

May 28, 2003    (KR) ............. 10-2003-0034109

(51) Int. Cl.
C07D 235/26    (2006.01)
C07D 235/28    (2006.01)
C07D 235/30    (2006.01)

(52) U.S. Cl. .................................. 548/305.1
(58) Field of Classification Search ............. 548/305.1
See application file for complete search history.

(56) References Cited

U.S. PATENT DOCUMENTS 5,466,817 A * 11/1995 Atwal ............... 548/305.1

OTHER PUBLICATIONS

Parker, J. Angina Pectoris: A Review of Current and Emerging Therapies. The American Journal of Managed Care, 2004, 10, S332-S338.*
Vilas-Boas, et al. Current Insights into the Modern Treatment of Decompensated Heart Failure. 2006, 87, 329-337.*
Gary J. Grover, Pharmacology of ATP-Sensitive Potassium Channel . . . , Can. J. Physiol. Pharmacol., vol. 75, pp. 309-315 (1997).
Gary D. Lopaschuk, et al, Manipulation of Energy Metabolism in the Heart, Science & Medicine, pp. 42-51, ((1997).
A.A. Starkov, "Mild" Uncoupling of Mitochondria, Bioscience Reports. vol. 17, No. 3, pp. 273-279, (1997).
Skulachev, Vladimir P., et al., Role of Uncoupled and Non-Coupled Oxidations in Maintenance . . . , Quarterly Reviews of Biophysics, vol. 29, pp. 169-202, (1996).
Okubo, Shinji, et al., Myocardial Preconditioning: Basic . . . , Molecular and Cellular Biochemistry, vol. 196, pp. 3-12, (1999).
Moreau, Jean-Luc, et al., Central Adenosine A . . . , Brain Research Reviews, vol. 31, pp. 65-82, (1999).

* cited by examiner

Primary Examiner—Kamal A. Saeed
Assistant Examiner—Shawquia Young
(74) Attorney, Agent, or Firm—Lucas & Mercanti, LLP

(57) ABSTRACT

The present invention relates to benzopyran derivatives substituted with a benzimidazole derivative, or pharmaceutically acceptable salts thereof, a preparation method of the same and pharmarceutical compositions containing them. Benzopyran derivatives substituted with a benzimidazole derivative, represented in Formula (1), have the function of protecting heart from ischemia-reperfusion without side effect like vasodilation, so that a pharmaceutical composition containing benzopyran derivatives substituted with a benzimidazole derivative or pharmaceutically acceptable salts thereof of the present invention as an effective ingredient can be effectively used for the protection of tissues influenced by ischemia-reperfusion, for example, for the protection of heart, nervous cells, brain, retinal cells, storage organs, etc. and for the treatment of diseases caused by ischemia-reperfusion.

11 Claims, No Drawings

BENZOPYRAN DERIVATIVES SUBSTITUTED WITH A BENZIMIDAZOLE DERIVATIVE, PHARMACEUTICALLY ACCEPTABLE SALTS THEROF, THEIR PREPARATIONS AND PHARMACEUTICAL COMPOSITIONS CONTAINING THEM

This patent application claims the benefit of priority from Korean Patent Application No. 10-2003-0034 109 filed May 28, 2003 through PCT Application Serial No. PCT/KR2004/001269 filed May 28, 2004 the contents of which are incorporated herein by reference.

FIELD OF THE INVENTION

The present invention relates to benzopyran derivatives substituted with a benzimidazole derivative, represented in <Formula 1>, pharmaceutically acceptable salts thereof, processes for preparing the same and a pharmaceutical compositions containing them as an effective ingredient having the function of protecting heart against damage caused by ischemia-reperfusion.

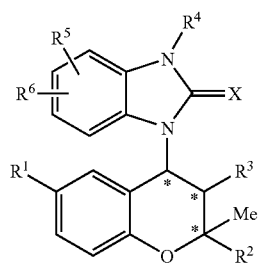

<Formula 1>

(Wherein, $R^1$, $R^2$, $R^3$, $R^4$, $R^5$, $R^6$ and * are as defined in the description.)

BACKGROUND

Ischemic heart disease results from myocardial ischemia developed by a serious deficiency of oxygen supply caused by interruption of blood flow to heart by a reason like arteriosclerosis (G. J. Grover, Can. J. Physiol. 75, 309, 1997; G. D. Lopaschuk et al. Science & Medicine 42, 1997). Myocardial ischemia induces pathological changes in cells progressively, leading to irreversible myocardial damage and even necrosis of cells and tissues, at last. In early stage when damage is reversible, irreversible damage might be prevented by reperfusion through surgical operations such as PTCA (percutaneous transluminal coronary angioplasty) and CABG (coronary artery bypass graft) or using thrombolytics, but the restoration of flow by reperfusion therapy is accompanied by a further injurious phenomenon called reperfusion injury (D. J. Hearse, Medicographia 18, 22, 1996). It is difficult to clearly separate ischemic injury from that mediated by reperfusion. Reperfusion injury is caused by sudden restoration of blood flow by reperfusion therapy, mainly due to reactive oxygen free radicals and calcium overload. Reperfusion injury includes a range of events, such as arrhythmia, vascular damage, myocardial dysfunction and serious neurocognitive dysfunction.

In order to delay damage by ischemia and minimize reperfusion injury, studies have actively been undergoing on pharmacotherapy using immune modulators, agents to suppress apoptosis, ion channel modulators, etc, artificial blood products to enhance the oxygen carrying potential of blood, and development of devices and operation procedures, but neither of them has been in commercial use, so far. As an ion channel modulators, an inhibitor of Na—H exchanger (NHE), an adenosine $A_1/A_2$ antagonist and a $K_{ATP}$ opener (ATP-sensitive potassium channel opener) draw our attention.

According to earlier reports, diazoxide, a $K_{ATP}$ opener, can reduce damage due to oxidative stress by suppressing the generation of oxygen free radicals in mitochondria by inducing oxidation of flavoprotein (A. A. Starkov, Biosci, Rep. 17, 273, 1997; V. P. Skulachev, Q. Rev. Biophus. 29, 169, 1996), and the opening of $K_{ATP}$ relates to the generation of antioxidant enzymes (S. Okubo et al., Mol. and cell Biochem, 196, 3, 1999) and the decrease of release of excitatory amino acids (J-L Moreau, G. Huber, Brain Res., 31, 65, 1999). The general $K_{ATP}$ openers have not only cardioprotective activity but also vasorelaxant activity, meaning that the relaxation of coronary and peripheral blood vessels drops blood pressure, so that blood flow to damaged tissues decreases, which is negative factor for cardioprotection. That is, vasorelaxation is a kind of side effect of those openers for heart protection.

$K_{ATP}$, which was first found in myocardium, is distributed in variety of organs and tissues such as β-cells of pancreas, smooth muscles, kidney and central nervous system, etc., so that it has been a major target for the development of a novel drug but, at the same time, it is hard to develop a novel medicine working selectively toward a specific organ or tissue. According to Atwal et al, the cardioprotective activity and vasorelaxant activity of $K_{ATP}$ are not related each other and benzopyranyl cyanoguanidines (BMS-180448) having a structure of <Formula 2> responses specifically to $K_{ATP}$ in heart, unlike conventional potassium channel openers. Those compounds have been confirmed to have comparatively weak vasorelaxant activity, so that they can protect heart without a significant hypotensive action, which provides a new chance for the development of a novel therapeutic agent for ischemic heart diseases.

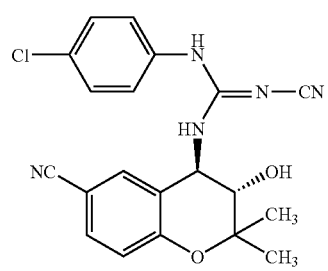

<Formula 2>

Thus, the inventors of the present invention synthesized benzopyran derivatives substituted with benzimidazole derivatives, in which the guanidinyl group substituted in the 4-position of benzopyran was cyclized to a benzene ring to form a benzimidazole ring. And the present inventors completed this invention by confirming that the compound of the invention had an excellent cardioprotective effect against the damage caused by ischemia-reperfusion, so that it can be effectively used as a protective agent or therapeutic agent for ischemia-reperfusion related diseases. Precisely, the compound can be used for the treatment of ischemic heart diseases such as myocardial infarction, unstable angina pectoris, etc. and for the protection of heart upon thrombolytic therapy or reperfusion therapy such as PTCA (percutaneous transluminal coronary angioplasty) and CABG (coronary artery bypass graft), and for the protection of ischemia-reperfusion related tissues such as nerve cells, brain, retinal cells, storage organs, etc.

SUMMARY OF THE INVENTION

It is an object of this invention to provide benzopyran derivatives substituted with benzimidazole derivatives, represented in <Formula 1>, or pharmaceutically acceptable salts thereof.

It is also an object of this invention to provide processes for preparing benzopyran derivatives substituted with benzimidazole derivatives, represented in <Formula 1>, or pharmaceutically acceptable salts thereof.

It is a further object of this invention to provide a pharmaceutical composition containing benzopyran derivatives substituted with benzimidazole derivatives, represented in <Formula 1>, or pharmaceutically acceptable salts of the same as an effective ingredient.

DETAILED DESCRIPTION OF PREFERRED EMBODIMENTS

In order to achieve the above object, the present invention provides benzopyran derivatives substituted with a benzimidazole derivative, pharmaceutically acceptable salts thereof, processes for preparing the same and a pharmaceutical composition containing them as an effective ingredient.

Hereinafter, the present invention is described in detail.

The present invention provides benzopyran derivatives substituted with benzimidazole derivatives, represented in <Formula 1>, or pharmaceutically acceptable salts thereof.

<Formula 1>

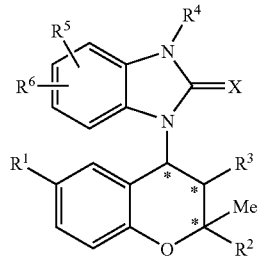

(Wherein,
X is O, S or NCN;
$R^1$ is $NO_2$, $NH_2$, H, CN, $NHCOCH_3$, $NHCOCF_3$ or $NHSO_2CH_3$;
$R^2$ is

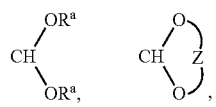

$CH_2OR^a$ or $CH_3$

Wherein,
$R^a$ is $C_1$~$C_4$ straight or branched alkyl;
Z is $C_2$~$C_6$ straight or branched alkyl;
$R^3$ is OH or $OCOCH_3$;
$R^4$ is $C_1$~$C_4$ straight or branched alkyl;
$R^5$ and $R^6$ are independently H, $C_1$~$C_4$ straight or branched alkyl, alkoxy or halogen;
* represents a chiral carbon.)

The present invention also provides, in addition to benzopyran derivatives represented in <Formula 1> and pharmaceutically acceptable salts, solvates and hydrates thereof.

Benzopyran derivatives of the present invention represented in <Formula 1> include not only a racemic mixture but also any diastereoisomer in which at least one carbon in the 2, 3, or 4-position is chiral. In <Formula 1>, if all the carbons in the 2, 3 and 4-position are chiral, 3,4-dihydro benzopyran compounds of the present invention are in the form of diastereoisomers as seen in $(I_1)$, $(I_2)$, $(I_3)$, and $(I_4)$ in the below <Formula 3>.

<Formula 3>

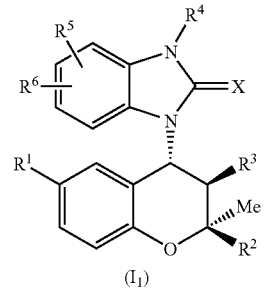

$(I_1)$

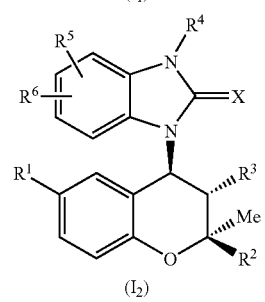

$(I_2)$

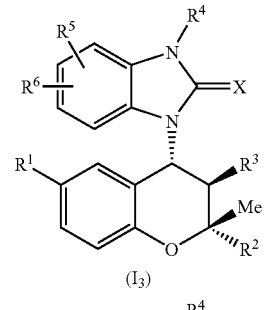

$(I_3)$

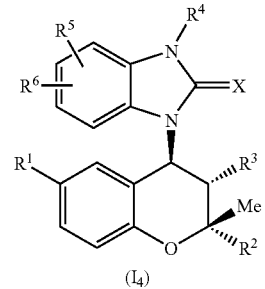

$(I_4)$ (Wherein, X, $R^1$, $R^2$, $R^3$, $R^4$, $R^5$ and $R^6$ are as defined in <Formula 1>.)

Preferable compounds of <Formula 1> include:

1)(2S, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;

2)(2R, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;

3)(2S, 3S, 4R)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;

4)(2R, 3S, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;

5)(2S, 3R, 4S)-6-amino-3,4-dihydro-3-hydroxy-2-dimethoxymethyl-2-methyl-4-(2,3-dihydro-2-cyanoimino-1H-benzimidazol-1-yl)-2H-1-benzopyran;

6)(2S, 3R, 4S)-6-nitro-3,4-dihydro-3-hydroxy-2-dimethoxymethyl-2-methyl-4-(2,3-dihydro-3-methyl-2-cyanoimino-1H-benzimidazol-1-yl)-2H-1-benzopyran;

7)(2S, 3R, 4S)-6-nitro-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran;

8)(2S, 3R, 4S)-6-amino-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran;

9) (2S, 3R, 4S)-6-nitro-3,4-dihydro-3-hydroxy-2-dimethoxymethyl-2-methyl-4-(2,3-dihydro-3,5,6-trimethyl-2-cyanoimino-1H-benzimidazol-1-yl)-2H-1-benzopyran;

10)(2S, 3R, 4S)-6-amino-3,4-dihydro-3-hydroxy-2-dimethoxymethyl-2-methyl-4-(2,3-dihydro-3,5,6-trimethyl-2-cyanoimino-1H-benzimidazol-1-yl)-2H-1-benzopyran;

11) (2S, 3R, 4S)-6-nitro-3,4-dihydro-3-acetoxy-2-dimethoxymethyl-2-methyl-4-(2,3-dihydro-2-cyanoimino-1H-benzimidazol-1-yl)-2H-1-benzopyran;

12)(2S, 3R, 4S)-6-amino-3,4-dihydro-3-acetoxy-2-dimethoxymethyl-2-methyl-4-(2,3-dihydro-2-cyanoimino-1H-benzimidazol-1-yl)-2H-1-benzopyran;

13)(2S, 3R, 4S)-6-acetamino-3,4-dihydro-3-hydroxy-2-dimethoxymethyl-2-methyl-4-(2,3-dihydro-2-cyanoimino-1H-benzimidazol-1-yl)-2H-1-benzopyran;

14)(2S, 3R, 4S)-6-acetamino-3,4-dihydro-3-acetoxy-2-dimethoxymethyl-2-methyl-4-(2,3-dihydro-2-cyanoimino-1H-benzimidazol-1-yl)-2H-1-benzopyran;

15)(2S, 3R, 4S)-6-benzoylamino-3,4-dihydro-3-hydroxy-2-dimethoxymethyl-2-methyl-4-(2,3-dihydro-2-cyanoimino-1H-benzimidazol-1-yl)-2H-1-benzopyran;

16)(2S, 3R, 4S)-6-(trifluoroacetyl)amino-3,4-dihydro-3-hydroxy-2-dimethoxymethyl-2-methyl-4-(2,3-dihydro-2-cyanoimino-1H-benzimidazol-1-yl)-2H-1-benzopyran;

17)(2S, 3R, 4S)-6-methanesulfonylamino-3,4-dihydro-3-hydroxy-2-dimethoxymethyl-2-methyl-4-(2,3-dihydro-2-cyanoimino-1H-benzimidazol-1-yl)-2H-1-benzopyran;

18) (2S, 3R, 4S)-6-nitro-3,4-dihydro-3-hydroxy-2-dimethoxymethyl-2-methyl-4-(2,3-dihydro-2-oxo-1H-benzimidazol-1-yl)-2H-1-benzopyran;

19)(2S, 3R, 4S)-6-amino-3,4-dihydro-3-hydroxy-2-dimethoxymethyl-2-methyl-4-(2,3-dihydro-2-oxo-1H-benzimidazol-1-yl)-2H-1-benzopyran;

20)(3R, 4S)-6-nitro-3,4-dihydro-3-hydroxy-2,2-dimethyl-4-(2,3-dihydro-2-oxo-1H-benzimidazol-1-yl)-2H-1-benzopyran;

21)(3R, 4S)-6-amino-3,4-dihydro-3-hydroxy-2,2-dimethyl-4-(2,3-dihydro-2-oxo-1H-benzimidazol-1-yl)-2H-1-benzopyran;

22)(2S, 3R, 4S)-6-nitro-3,4-dihydro-3-hydroxy-2-dimethoxymethyl-2-methyl-4-(2,3-dihydro-2-thioxo-1H-benzimidazol-1-yl)-2H-1-benzopyran;

23)(3R, 4S)-6-nitro-3,4-dihydro-3-hydroxy-2,2-dimethyl-4-(2,3-dihydro-2-thioxo-1H-benzimidazol-1-yl)-2H-1-benzopyran;

24)(3R, 4S)-6-amino-3,4-dihydro-3-hydroxy-2,2-dimethyl-4-(2,3-dihydro-2-thioxo-1H-benzimidazol-1-yl)-2H-1-benzopyran;

25)(2S, 3R, 4S)-6-nitro-3,4-dihydro-3-hydroxy-2-diethoxymethyl-2-methyl-4-(2,3-dihydro-2-cyanoimino-1H-benzimidazol-1-yl)-2H-1-benzopyran;

26)(2S, 3R, 4S)-6-nitro-3,4-dihydro-3-hydroxy-2-methoxymethyl-2-methyl-4-(2,3-dihydro-2-cyanoimino-1H-benzimidazol-1-yl)-2H-1-benzopyran;

27) (2S, 3R, 4S)-6-amino-3,4-dihydro-3-hydroxy-2-methoxymethyl-2-methyl-4-(2,3-dihydro-2-cyanoimino-1H-benzimidazol-1-yl)-2H-1-benzopyran;

28)(2S, 3R, 4S)-6-nitro-3,4-dihydro-3-hydroxy-2-methoxymethyl-2-methyl-4-(2,3-dihydro-2-cyanoimino-1H-6-methylbenzimidazol-1-yl)-2H-1-benzopyran;

29)(2S, 3R, 4S)-6-nitro-3,4-dihydro-3-hydroxy-2-([1,3]dioxan-2-yl)-2-methyl-4-(2,3-dihydro-2-cyanoimino-1H-benzimidazol-1-yl)-2H-1-benzopyran;

30)(2S, 3R, 4S)-6-amino-3,4-dihydro-3-hydroxy-2-([1,3]dioxan-2-yl)-2-methyl-4-(2,3-dihydro-2-cyanoimino-1H-benzimidazol-1-yl)-2H-1-benzopyran;

31)(2S, 3R, 4S)-6-nitro-3,4-dihydro-3-hydroxy-2-([1,3]dioxolan-2-yl)-2-methyl-4-(2,3-dihydro-2-cyanoimino-1H-benzimidazol-1-yl)-2H-1-benzopyran; and 32)(2S, 3R, 4S)-6-nitro-3,4-dihydro-3-hydroxy-2-([1,3]-5,5-dimethyldioxan-2-yl)-2-methyl-4-(2,3-dihydro-2-cyanoimino-1H-benzimidazol-1-yl)-2H-1-benzopyran.

The compounds of <Formula 1> of the present invention are available in the form of pharmaceutically acceptable salts. And acid addition salts prepared by pharmaceutically acceptable free acids or metal salts a re useful.

The acid salts of the compounds according to the present invention can be prepared in the customary manner, for example by dissolving the compound of <Formula 1> in excess aqueous free acid solution and precipitating the salt using a water-miscible organic solvent, such as methanol, ethanol, acetone or acetonitrile. It is also possible to prepare the acid salt by heating equivalent amounts of the compound of <Formula 1> and an free acid in water or alcohol, such as glycol monomethyl ether, and then evaporating the mixture to dryness or filtering off the precipitated salt with suction. Whether it is inorganic or organic, a free acid can be used if it is pharmaceutically acceptable. Examples of the inorganic free acid include hydrochloric acid, hydrobromic acid, sulfuric acid, and phosphoric acid. Available organic free acids are exemplified by citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid and aspartic acid.

Also, the compounds of <Formula 1> may be in the form of pharmaceutically acceptable alkali metal or alkaline earth metal salts. The alkali metal or alkaline earth metal salts of the compounds of <Formula 1> can be obtained, for example, by dissolving the compound of <Formula 1> in excess alkali metal or alkaline earth metal hydroxide solution, filtering off the undissolved materials and evaporating the filterate to dryness. Sodium, potassium or calcium salts are pharmaceutically suitable.

The present invention also provides processes for preparing benzopyran derivatives substituted with benzimidazole derivatives of <Formula 1>.

Particularly, the present invention provides a process for preparing a compound of Formula (I), which is shown in <Scheme 1>. Reaction of a compound (III) with a diamine compound (IV) in the presence of a proper metal salt gives a compound of Formula (V). Then, cyclization of compound (IV) using an appropriate reagent for introducing an X group affords a compound (I'). Finally, a benzopyran compound substituted with a benzimidazole (I) is prepared by changing substituents $R^1$, $R^2$, $R^3$, $R^4$, $R^5$ and $R^6$. This is defined as 'preparation process 1' hereafter.

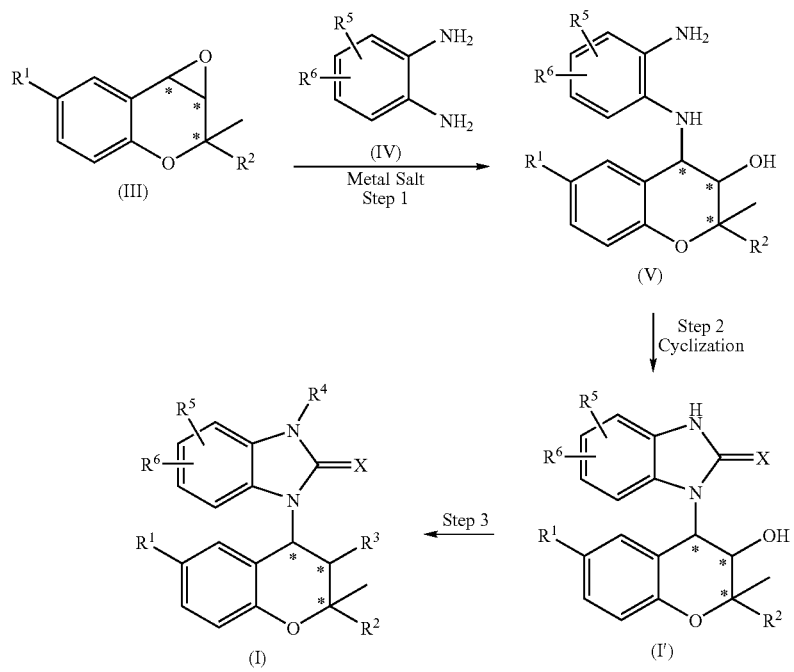

(Wherein, X, $R^1$, $R^2$, $R^3$, $R^4$, $R^5$, $R^6$ and * are as defined in <Formula 1>.)

The present invention also provides another process for preparing a compound of Formula (I) which is shown in <Scheme 2>. cyclization of a diamine compound (IV) using proper reagent gives a compound of Formula (VI). Then, epoxide ring opening of compound (III) is accomplished by reaction with a compound (VI) in the presence of a proper base, giving a compound of Formula (I'). Finally, a benzopyran compound substituted with a benzimidazole (I) is prepared by introducing substituents $R^1$, $R^2$, $R^3$, $R^4$, $R^5$ and $R^6$. This is defined as 'preparation process 2' hereafter.

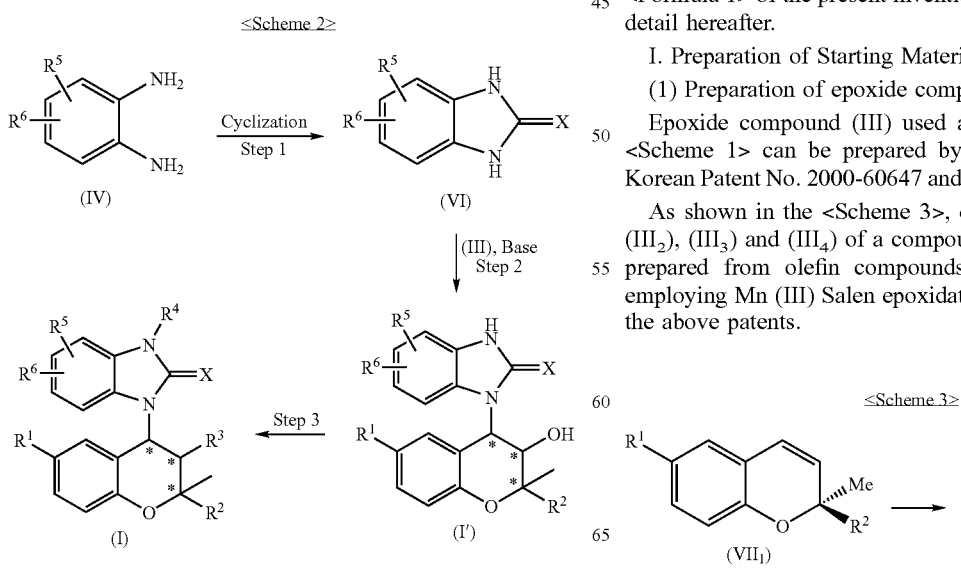

(Wherein, X, $R^1$, $R^2$, $R^3$, $R^4$, $R^5$, $R^6$ and * are as defined in <Formula 1>.)

In the present invention, a compound of <Formula 1> can be prepared in the form of an individual diastereomer from the corresponding diastereomer of starting material. Each diastereomer can also be obtained by separating the diastereomeric mixture of compound (I) prepared from a diasteremeric mixture of starting material. The separation of diastereomers can be carried out by column chromatography or recrystallization.

The preparation processes for benzopyran derivatives substituted with a benzimidazole derivative represented in <Formula 1> of the present invention are illustrated in more detail hereafter.

I. Preparation of Starting Material (1) Preparation of epoxide compound (III)

Epoxide compound (III) used as a starting material in <Scheme 1> can be prepared by processes described in Korean Patent No. 2000-60647 and U.S. Pat. No. 6,323,238.

As shown in the <Scheme 3>, each diastereomer ($III_1$), ($III_2$), ($III_3$) and ($III_4$) of a compound (III) can be possibly prepared from olefin compounds ($VII_1$) and ($VII_2$) by employing Mn (III) Salen epoxidation catalyst described in the above patents.

<Scheme 3>

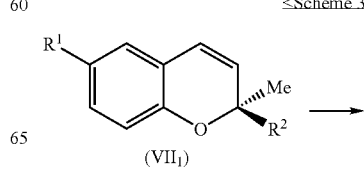

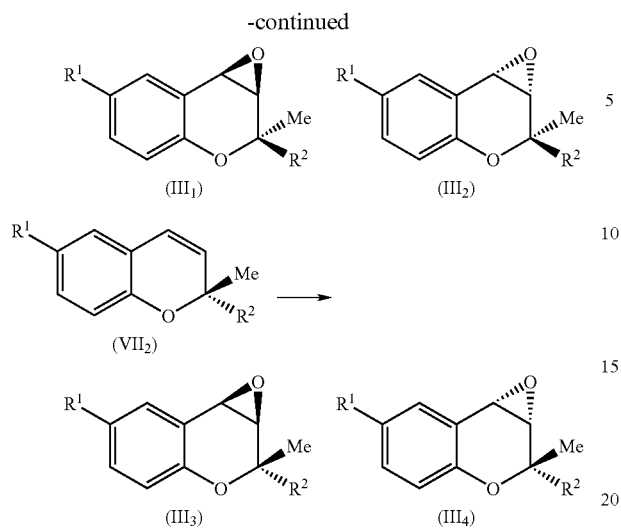

(Wherein, R¹ and R² are as defined in <Formula 1>.)

II. Preparation Process 1

The preparation process for a compound of Formula (I) represented in <Scheme 1> comprises the following steps:

1) preparing compound (V) by reaction of epoxide compound (III) with diamine compound (IV) in the presence of a proper metal salt in proper solvent;
2) preparing compound (I') by cyclization of diamine compound (V) using an appropriate reagent for introducing X group; and
3) preparing compound (I) by changing substituents of the compound (I').

In the step 1) is a reaction of epoxide compound (III) with diamine compound (IV) in the presence of a proper metal salt in proper solvent.

As a metal salt, $Mg(ClO_4)_2$, $CoCl_2$, $LiClO_4$, $NaClO_4$, $CaCl_2$, $ZnCl_2$, $LiBF_4$ or $Zn(Tf)_2$ can be used. As a solvent, acetonitrile, tetrahydrofuran or dimethylformamide can be used and acetonitrile is preferred. Reaction temperature ranges from room temperature to the boiling point of the solvent.

In case that an individual stereoisomer of epoxide compound (III) is used as starting material, the stereroisomer with a stereochemistry corresponding to the stereoisomer used as starting material will be obtained. As shown in the below <Scheme 4>, compounds ($V_1$), ($V_2$), ($V_3$) and ($V_4$) are prepared from each epoxide compound ($III_1$), ($III_2$), ($III_3$) and ($III_4$).

<Scheme 4>

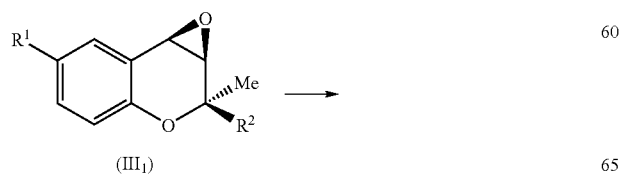

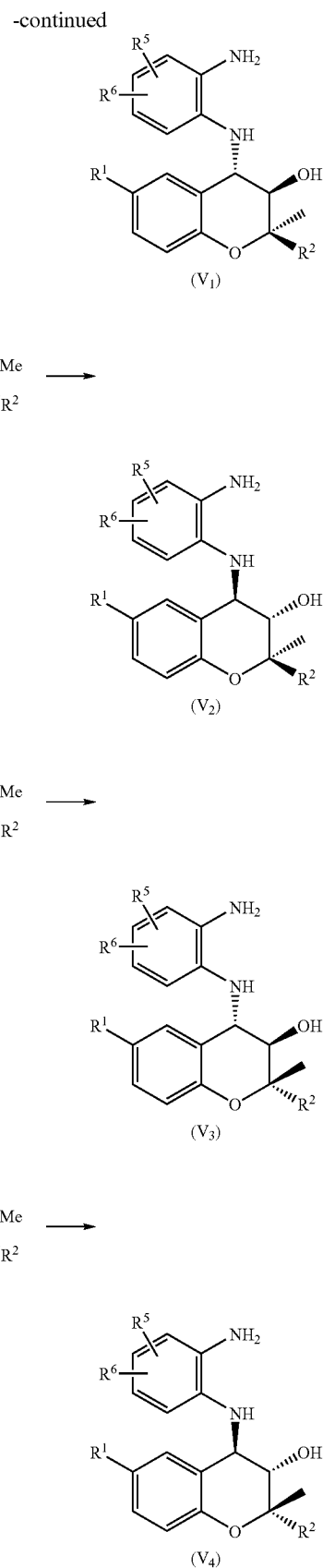

As shown in <Scheme 5>, in the above step 2), the compound of <formula 1> in which X is O, S or NCN can be prepared from a compound (V) by performing a cyclization using an appropriate reagent.

a mixture of water and methanol and reaction temperature ranges from room temperature to the boiling point of the solvent.

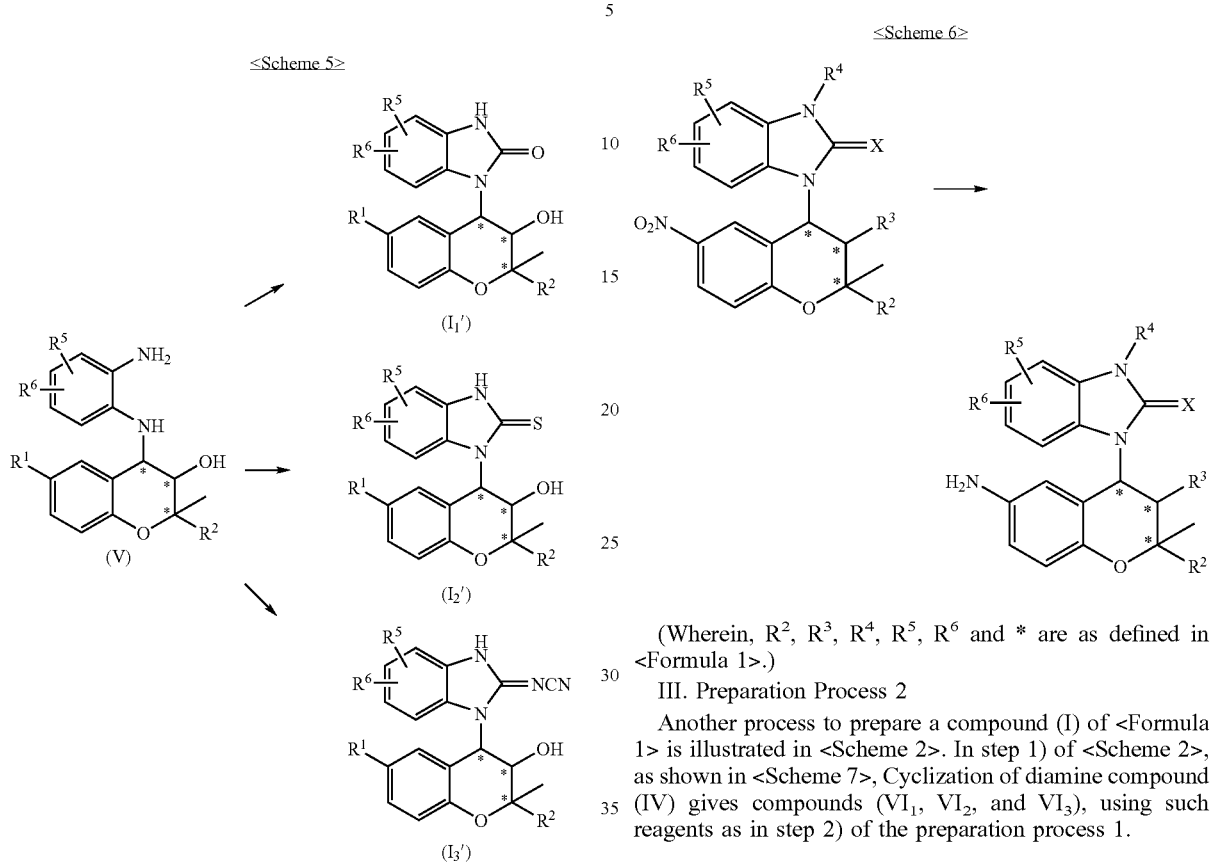

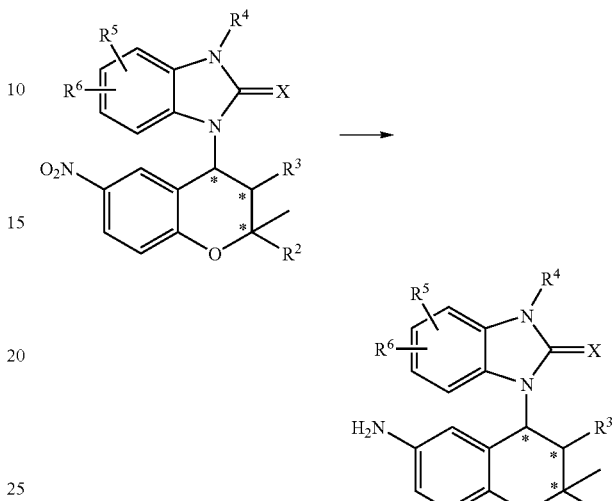

(Wherein, $R^2$, $R^3$, $R^4$, $R^5$, $R^6$ and * are as defined in <Formula 1>.)

III. Preparation Process 2

Another process to prepare a compound (I) of <Formula 1> is illustrated in <Scheme 2>. In step 1) of <Scheme 2>, as shown in <Scheme 7>, Cyclization of diamine compound (IV) gives compounds ($VI_1$, $VI_2$, and $VI_3$), using such reagents as in step 2) of the preparation process 1.

(Wherein, $R^1$, $R^2$, $R^5$, $R^6$ and * are as defined in <Formula 1>.)

The compound of formula ($I_1$') in which X is O can be prepared by using carbonyl transfer reagent derived from phosgene such as phosgene, urea, dimethyl carbonate, carbonyldiimidazole, triphosgene, 1,1'-carbonyl-di-1,2,4-triazole, 1-disuccinimidyl carbonate, di-2-pyridyl carbonate, etc.

The compound of formula ($I_2$') in which X is S can be prepared by using thiocarbonyl transfer reagent derived from thiophosgene such as thiophosgene, thiourea, 1,1'-thiocarbonyldiimidazole, 1,1'-thiocarbonyldi-1,2,4-triazole, di-2-pyridyl thiocarbonate, 1,1'-thiocarbonyl-2,2'-pyridone, etc.

The compound of formula ($I_3$'), in which X is NCN can be prepared by using diphenyl cyanocarbonimidate or N-cyanodithioiminocarbonate.

In the above step 3), a compound (I) of <Formula 1> is prepared by changing substituents $R^1$, $R^2$, $R^3$, $R^4$, $R^5$ and $R^6$ by alkylation, acylation, reduction, or substitution, etc.

For example, as shown in <Scheme 6>, if $R^1$ of a compound (I) is amino group, the compound can be prepared by reducing nitro group, for which hydrogenation is performed using a metal catalyst such as platinum, palladium on carbon (Pd/C) or Raney-nickel in proper solvent. Alternatively, a nitro group can be reduced by a reducing agent like $NaBH_4$ in the presence of $CuSO_4$, $Cu(OAc)_2$, $CoCl_2$, $SnCl_2$ or $NiCl_2$. In this reaction, preferable solvent is

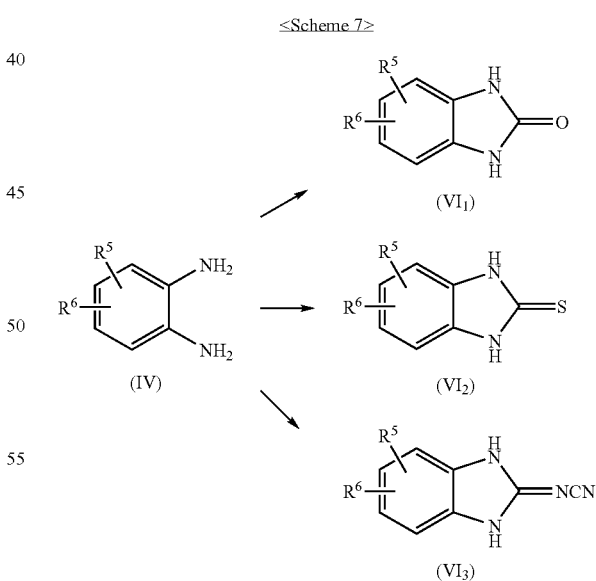

In step 2), a compound (I') is prepared by epoxide ring opening, in which a compound (VI) is reacted with epoxide compound (III) in the presence of base. Both inorganic base such as sodium hydride, potassium t-butoxide, sodium methoxide, etc. and organic base such as 1,8-diazabicyclo [5.4.0]undec-7-ene (DBU), etc, can be used.

In step 3), a compound (I) is prepared by changing substituents as described in the preparation process 1.

The present invention further provides a pharmaceutical composition for cardioprotection containing benzopyran derivatives substituted with a benzimidazole derivative, represented in <Formula 1>, or pharmaceutically acceptable salts thereof as an effective ingredient.

When tested in ischemic heart models of Langendorff using isolated rat hearts, compounds of the present invention significantly prolong the time to contracture (TTC), an index of heart protection, and improve recovery of the cardiac function (left ventricular developed pressure×heart rate, LVDP×HR) after reperfusion, but reduce release of lactate dehydrogenase (LDH), an index for cell damage, which are similar or superior to cardioprotecting activity of BMS-180448, a control. In ischemic myocardium models using anesthetized rat, compounds of the present invention also show similar antiischemic activity to BMS-180448. In the tests with blood vessels isolated from a white rat, the compounds of the present invention shows better cardioselective antiischemic activity than BMS-180448 owing to their minor vasorelaxant activity.

In conclusion, the compounds of the present invention do not drop blood pressure owing to their minor vasorelaxant activity but have excellent antiischemic activity. Therefore, the compounds of the invention can be effectively used not only for the protection of heart but also for the prevention or the treatment of ischemic heart diseases such as myocardial infarction and unstable angina pectoris and ischemia-reperfusion related diseases caused by thrombolytics or reperfusion therapy like PTCA (percutaneous transluminal coronary angioplasty) and CABG (coronary artery bypass graft), decrease of myocardial contractility, myocardial injury, change of energy metabolism and decline of cognitive capability. In addition, the compounds of the present invention can be used as a protective agent against brain injury, a protective agent for retinal cells or organs for long-term storage such as heart, kidney, liver and tissues, or a treating agent for ischemia-reperfusion related diseases.

EXAMPLES

In the following the invention is described in more detail with reference to examples. These examples are intended for illustration only and are not to be construed as any limitation.

In the present invention, infrared spectroscopy, nuclear magnetic resonance spectroscopy, mass spectroscopy, liquid chromatography, x-ray crystallography, polarimetry were used along with the comparison of estimated results of elemental analysis of the representative compounds with analyzed results of them in order to confirm their molecular structures.

Example 1

Preparation of (2S, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran <Step 1>Preparation of (2S, 3R, 4S)-6-nitro-3,4-dihydro-3-hydroxy-2-dimethoxymethyl-2-methyl-4-[(2-aminophenyl)amino]-2H-1-benzopyran 950 mg (3.38 mmol) of epoxide compound (2S, 3R, 4R)-6-nitro-3,4-dihydro-3,4-epoxy-2-dimethoxymethyl-2-methyl-2H-1-benzopyran and 370 mg (3.38 mmol) of 1,2-phenylinediamine were dissolved in 3 ml of acetonitrile ($CH_3CN$), then 754 mg (3.38 mmol) of magnesium perchlorate [$Mg(ClO_4)_2$] was added thereto. The reaction is stirred at room temperature for 2 hours, 10 ml of saturated $NaHCO_3$ solution was added, and aqueous layer was extracted with 30 ml of ethyl acetate. Combined organic layer was dried over anhydrous $MgSO_4$, filtered and concentrated under reduced pressure. The residue was purified by column chromatography (hexane:ethyl acetate=1:1), to give 670 mg (yield: 51%) of the target compound.

$^1$H NMR (200 MHz, $CDCl_3$) δ 1.48(s, 3H), 3.53(s, 3H), 3.55(s, 3H), 4.08(d, 1H), 4.47(s, 1H), 4.62(d, 1H), 6.79(m, 5H), 8.06(dd, 1H), 8.32(d, 1H)

<Step 2> Preparation of (2S, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran 590 mg (1.52 mmol) of the compound obtained in the above step 1 was dissolved in 6 ml of i-PrOH, then 360 mg (1.52 mmol) of diphenyl cyanocarbonimidate and 424 µl (3.04 mmol) of triethylamine were added thereto. The reaction was stirred and refluxed for 12 hours, 30 ml of saturated $NaHCO_3$ solution was added, aqueous layer was extracted with 40 ml of ethyl acetate. Combined organic layer was washed with brine and dried over anhydrous $MgSO_4$, and concentrated under reduced pressure. The residue was purified by silica gel column chromatography (hexane:ethyl acetate=1:1), to give 420 mg (yield: 64%) of the target compound.

$^1$H NMR (200 MHz, $CDCl_3$) δ 1.66(s, 3H), 3.50(s, 3H), 3.55(s, 3H), 4.21(d, 1H), 4.56(s, 1H), 6.11(d, 1H), 6.25(d, 1H), 6.90(m, 1H), 7.11(m, 2H), 7.28(m, 1H), 7.76(d, 1H), 8.11(dd, 1H)

Example 2

Preparation of (2R, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran <Step 1> Preparation of (2R, 3R, 4S)-6-nitro-3,4-dihydro-3-hydroxy-2-dimethoxymethyl-2-methyl-4-[(2-aminophenyl)amino]-2H-1-benzopyran 540 mg (1.92 mmol) of epoxide compound (2R, 3R, 4R)-6-nitro-3,4-dihydro-3,4-epoxy-2-dimethoxymethyl-2-methyl-2H-1-benzopyran and 208 mg (1.92 mmol) of 1,2-phenylinediamine were reacted in analogy to the procedure described in step 1 of the example 1, to give 404 mg (yield: 54%) of the target compound.

$^1$H NMR (200 MHz, $CDCl_3$) δ 1.43(s, 3H), 3.50(s, 3H), 3.55(s, 3H), 4.14(d, 1H), 4.45(s, 1H), 4.49(d, 1H), 6.75(m, 5H), 8.09(dd, 1H), 8.32(d, 1H)

<Step 2> Preparation of (2R, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran Reaction of 404 mg (1.04 mmol) of the compound prepared in the above step 1 was performed in analogy to the procedure described in the step 2 of the example 1, to give 306 mg (yield: 67%) of the target compound.

$^1$H NMR (200 MHz, $CDCl_3$) δ 1.49(s, 3H), 3.62(s, 3H), 3.64(s, 3H), 4.51(s, 1H), 4.78(d, 1H), 5.90(d, 1H), 6.40(d, 1H), 6.9-7.4(m, 4H), 7.79(d, 1H), 8.14(dd, 1H)

Example 3

Preparation of (2S, 3S, 4R)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran <Step 1> Preparation of (2S, 3S, 4R)-6-nitro-3,4-dihydro-3-hydroxy-2-dimethoxymethyl-2-methyl-4-[(2-aminophenyl)amino]-2H-1-benzopyran Reaction of 2 g (7.11 mmol) of epoxide compound (2S, 3S, 4S)-6-nitro-3,4-dihydro-3,4-epoxy-2-dimethoxymethyl-2-methyl-2H-1-benzopyran with 1.15 g (10.7 mmol) of 1,2-phenylinediamine were performed in analogy to the procedure described in step 1 of the example 1, to give 2.08 g (yield: 75%) of the target compound.

$^1$H NMR (200 MHz, CDCl$_3$) δ 1.36(s, 3H), 3.58(s, 3H), 3.59(s, 3H), 4.23(d, 1H), 4.41(s, 1H), 4.51(d, 1H), 6.72-6.78 (m, 4H), 6.90(d, 1H), 8.03(dd, 1H), 8.34(d, 1H) Mass: 389, 296, 119, 108, 75

<Step 2> Preparation of (2S, 3S, 4R)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran Reaction of 1.51 g (3.88 mmol) of the compound prepared in the above step 1 was performed in analogy to the procedure described in step 2 of the example 1, to give 506 g (yield: 30%) of the target compound.

$^1$H NMR (200 MHz, CDCl$_3$) δ 1.49(s, 3H), 3.62(s, 3H), 3.64(s, 3H), 4.50(s, 1H), 4.77(d, 1H), 5.90(d, 1H), 6.37(d, 1H), 6.92(t, 1H), 7.06-7.14(m, 2H), 7.29(d, 1H), 7.76(d, 1H), 8.12(dd, 1H) Mass: 439, 250, 190, 158, 75

Example 4

Preparation of (2R, 3S, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran <Step 1> Preparation of (2R, 3S, 4S)-6-nitro-3,4-dihydro-3-hydroxy-2-dimethoxymethyl-2-methyl-4-[(2-aminophenyl)amino]-2H-1-benzopyran Reaction of 1.50 g (5.33 mmol) of epoxide compound (2R, 3R, 4R)-6-nitro-3,4-dihydro-3,4-epoxy-2-dimethoxymethyl-2-methyl-2H-1-benzopyran with 692 mg (6.40 mmol) of 1,2-phenylinediamine was performed in analogy to the procedure described in step 1 of the example 1, to give 1.74 g (yield: 84%) of the target compound.

$^1$H NMR (200 MHz, CDCl$_3$) δ 1.48(s, 3H), 3.53(s, 3H), 3.55(s, 3H), 3.88(br-s, OH), 4.09(d, 1H), 4.48(s, 1H), 4.64 (br-s, 1H), 6.71-6.97(m, 5H), 8.06(dd, 1H), 8.32(d, 1H) Mass: 388, 295, 119, 108, 75

<Step 2> Preparation of (2R, 3S, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran Reaction of 1.74 g (4.47 mmol) of the compound prepared in the above step 1 was performed in analogy to the procedure described in step 2 of the example 1, to give 1.12 g (yield: 57%) of the target compound.

$^1$H NMR (200 MHz, CDCl$_3$) δ 1.66(s, 3H), 3.50(s, 3H), 3.56(s, 3H), 4.24(d, 1H), 4.57(s, 1H), 6.14(d, 1H), 6.27(d, 1H), 6.90(t, 1H), 7.05-7.13(m, 2H), 7.31(d, 1H), 7.76(d, 1H), 8.14(dd, 1H) Mass: 439, 250, 190, 75

Example 5

Preparation of (2S, 3R, 4S)-6-amino-3,4-dihydro-3-hydroxy-2-dimethoxymethyl-2-methyl-4-(2,3-dihydro-2-cyanoimino-1H-benzimidazol-1-yl)-2H-1-benzopyran 150 mg (0.34 mmol) of the compound obtained in the example 1 was dissolved in 3 ml of methanol, to which 20 mg of 10% Pd/C was added. The reaction was stirred for 5 hours at room temperature under 3 atm of hydrogen gas. The reaction solution was filtered with celite pad to eliminate solid substances, the filterate concentrated under reduced pressure. The residue was purified by silica gel column chromatography (hexane:ethyl acetate=2:1), to give 120 mg (yield: 80%) of the target compound.

$^1$H NMR (200 MHz, CDCl$_3$) δ 1.55(s, 3H), 3.49(br-s, 2H, NH2), 3.53(s, 3H), 3.57(s, 3H), 4.23(d, 1H), 4.59(s, 1H), 5.81(d, 1H), 6.18(d, 1H), 6.48(d, 1H), 6.60(dd, 1H)t 6.78(d, 1H), 6.91(dd, 1H), 7.07(dd, 1H), 7.24(d, 1H)

Example 6

Preparation of (2S, 3R, 4S)-6-nitro-3,4-dihydro-3-hydroxy-2-dimethoxymethyl-2-methyl-4-(2,3-dihydro-3-methyl-2-cyanoimino-1H-benzimidazol-1-yl)-2H-1-benzopyran 400 mg (0.91 mmol) of the compound obtained in example 1 was dissolved in 5 ml of DMF, then 250 mg (1.82 mmol) of K$_2$CO$_3$ and 170 mg (1.18 mmol) of CH$_3$I were added thereto. The reaction was stirred at room temperature for 12 hours, 30 ml of saturated NaHCO$_3$ solution was added, and aqueous layer was extracted with 50 ml of ethyl acetate. Organic layer was washed with brine and dried over anhydrous MgSO$_4$, concentrated under reduced pressure. The residue was purified by silica gel column chromatography (hexane:ethyl acetate=1:1), to give 390 mg (yield: 95%) of the target compound.

$^1$H NMR (200 MHz, CDCl$_3$) δ 1.65 (s, 3H), 3.50 (s, 3H), 3.55 (s, 3H), 4.56 (s, 1H), 6.23 (d, 1H), 6.52 (d, 1H), 6.92 (m, 2H), 6.96 (d, 2H), 7.06 (d, 2H), 7.82 (d, 1H), 8.15 (dd, 1H)

Example 7

Preparation of (2S, 3R, 4S)-6-nitro-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran <Step 1> Preparation of (2S, 3R, 4S)-6-nitro-3,4-dihydro-3-hydroxy-2-dimethoxymethyl-2-methyl-4-[(2-amino-4,5-dimethylphenyl)amino]-2H-1-benzopyran Reaction of 480 mg (1.71 mmol) of epoxide compound (2S, 3R, 4R)-6-nitro-3,4-dihydro-3,4-epoxy-2-dimethoxymethyl-2-methyl-2H-1-benzopyran with 232 mg (1.71 mmol) of 4,5-dimethyl-1,2-phenylinediamine was performed in analogy to the procedure described in step 1 of the example 1, to give 307 mg (yield: 43%) of the target compound.

$^1$H NMR (200 MHz, CDCl$_3$) δ 1.47(s, 3H), 2.16(s, 3H), 2.19(s, 3H), 3.53(s, 3H), 3.55(s, 3H), 4.08(d, 1H), 4.47(s, 1H), 4.56(d, 1H), 6.61(s, 1H), 6.65(s, 1H), 6.93(d, 1H), 8.07(dd, 1H), 8.34(d, 1H)

<Step 2> Preparation of (2S, 3R, 4S)-6-nitro-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran Reaction of 110 mg (0.26 mmol) of the compound prepared in the above step 1 was performed in analogy to the procedure described in step 2 of the example 1, to give 74 mg (yield: 58%) of the target compound.

$^1$H NMR (200 MHz, CDCl$_3$) δ 1.67(s, 3H), 2.07(s, 3H), 2.20(s, 3H), 3.51(s, 3H), 3.55(s, 3H), 4.20(d, 1H), 4.55(s, 1H), 6.01(s, 1H), 6.06(d, 1H), 7.04(d, 1H), 7.07(s, 1H), 7.74(d, 1H), 8.13(dd, 1H)

Example 8

Preparation of (2S, 3R, 4S)-6-amino-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran Reaction of 210 mg (0.43 mmol) of a nitro compound prepared in example 7 was performed in analogy to the procedure described in the example 5, to give 177 mg (yield: 91%) of the target compound.

$^1$H NMR (200 MHz, CDCl$_3$) δ 1.54(s, 3H), 2.15(s, 3H), 2.17(s, 3H), 3.52(s, 3H), 3.54(s, 3H), 4.25(d, 1H), 4.66(s, 1H), 6.14(d, 1H), 6.17(d, 1H), 6.39(s, 1H), 6.56(dd, 1H), 6.74(d, 1H), 7.32(s, 1H)

Example 9

Preparation of (2S, 3R, 4S)-6-nitro-3,4-dihydro-3-hydroxy-2-dimethoxymethyl-2-methyl-4-(2,3-dihydro-3,5,6-trimethyl-2-cyanoimino-1H-benzimidazol-1-yl)-2H-1-benzopyran Reaction of 180 mg (0.37 mmol) of the compound prepared in example 7 was performed in analogy to the procedure described in the example 6, to give 144 mg (yield: 81%) of the target compound.

$^1$H NMR (200 MHz, CDCl$_3$) δ 1.65(s, 3H), 2.07(s, 3H), 2.26(s, 3H), 3.51(s, 3H), 3.54(s, 3H), 3.87(s, 3H), 4.55(s, 1H), 5.98(s, 1H), 6.44(d, 1H), 6.94(s, 1H), 7.05(d, 1H), 7.80(d, 1H), 8.17(dd, 1H)

Example 10

Preparation of (2S, 3R, 4S)-6-amino-3,4-dihydro-3-hydroxy-2-dimethoxymethyl-2-methyl-4-(2,3-dihydro-3,5,6-trimethyl-2-cyanoimino-1H-benzimidazol-1-yl)-2H-1-benzopyran Reaction of 70 mg (0.15 mmol) of a nitro compound prepared in example 9 was performed in analogy to the procedure described in the example 5, to give 58 mg (yield: 89%) of the target compound.

$^1$H NMR (200 MHz, CDCl$_3$) δ 1.56(s, 3H), 2.12(s, 3H), 2.28(s, 3H), 3.53(s, 3H), 3.59(s, 3H), 3.80(s, 3H), 4.17(t, 1H), 4.62(s, 1H), 6.24(s, 1H), 6.26(d, 1H), 6.64(dd, 1H), 6.78(d, 1H), 6.91(s, 1H)

Example 11

Preparation of (2S, 3R, 4S)-6-nitro-3,4-dihydro-3-acetoxy-2-dimethoxymethyl-2-methyl-4-(2,3-dihydro-2-cyanoimino-1H-benzimidazol-1-yl)-2H-1-benzopyran 388 mg (0.88 mmol) of the compound obtained in the example 1 was dissolved in 4 ml of methylenechloride, then 83 μl (0.88 mmol) of acetic anhydride, 0.18 ml (1.32 mmol) of triethylamine and 32 mg (0.26 mmol) of 4-dimethylaminopyridine were added thereto. The reaction was stirred at room temperature for 2 hours, 30 ml of saturated NaHCO$_3$ solution was added, aqueous layer was extracted with 60 ml of methylenechloride. Organic layer was washed with brine and dried over anhydrous MgSO$_4$, concentrated under reduced pressure. The residue was purified by silica gel column chromatography (hexane:ethyl acetate=2:1), to give 376 mg (yield: 89%) of the target compound.

$^1$H NMR (200 MHz, CDCl$_3$) δ 1.49(s, 3H), 2.10(s, 3H), 3.52(s, 3H), 3.55(s, 3H), 4.63(s, 1H), 5.62(d, 1H), 6.24(d, 1H), 6.31(d, 1H), 6.91-7.24(m, 3H), 7.33(d, 1H), 7.70(d, 1H), 8.13(dd, 1H) Mass: 481(M+)

Example 12

Preparation of (2S, 3R, 4S)-6-amino-3,4-dihydro-3-acetoxy-2-dimethoxymethyl-2-methyl-4-(2,3-dihydro-2-cyanoimino-1H-benzimidazol-1-yl)-2H-1-benzopyran 196 mg (0.41 mmol) of a nitro compound obtained in the example 11 was dissolved in 10 ml of methanol, to which 98 mg of Raney-Ni was added. The reaction was stirred for 15 hours at room temperature under 3 atm of hydrogen gas. The reaction solution was filtered to eliminate Ni, followed by concentration under reduced pressure. The residue was purified by silica gel column chromatography (hexane:ethyl acetate=1:2), to give 70 mg (yield: 38%) of the target compound.

$^1$H NMR (200 MHz, CDCl$_3$) δ 1.40(s, 3H), 2.06(s, 3H), 3.35(br-s, 2H, -NH2), 3.47(s, 3H) 3.55(s, 3H), 4.56(s, 1H), 5.63(d, 1H), 6.05(d, 1H), 6.12(d, 1H), 6.53(d, 1H), 6.59(dd, 1H), 6.81(d, 1H), 6.96(dd, 1H), 7.11(dd, 1H), 7.29(d, 1H)

Example 13

Preparation of (2S, 3R, 4S)-6-acetamino-3,4-dihydro-3-hydroxy-2-dimethoxymethyl-2-methyl-4-(2,3-dihydro-2-cyanoimino-1H-benzimidazol-1-yl)-2H-1-benzopyran Reaction of 100 mg (0.24 mmol) of the compound prepared in example 5 was performed in analogy to the procedure described in the example 11, to give 62 mg (yield: 57%) of the target compound.

$^1$H NMR (200 MHz, CDCl$_3$) δ 1.49(s, 3H), 1.93(s, 3H), 3.44(s, 3H), 3.46(s, 3H), 4.13(dd, 1H), 4.52(s, 1H), 5.81(d, 1H), 6.34(d, 1H), 6.71(d, 1H), 6.80-6.87(m, 2H), 7.01(dd, 1H), 7.20(d, 1H), 7.68(dd, 1H), 8.59(s, 1H, —NH), 12.26(s, 1H, —NH)

Example 14

Preparation of (2S, 3R, 4S)-6-acetamino-3,4-dihydro-3-acetoxy-2-dimethoxymethyl-2-methyl-4-(2,3-dihydro-2-cyanoimino-1H-benzimidazol-1-yl)-2H-1-benzopyran 88 mg (0.21 mmol) of the compound obtained in example 5 was dissolved in methylenechloride, then 61 μl (0.64 mmol) of acetic anhydride, 120 μl (0.86 mmol) of triethylamine and 8 mg (0.06 mmol) of 4-dimethylaminopyridine were added thereto. The reaction was stirred at room temperature for 12 hours, saturated NaHCO$_3$ solution was added, aqueous layer was extracted with methylenechloride. Organic layer was washed with brine and dried over anhydrous MgSO$_4$, concentrated under reduced pressure. The residue was purified by silica gel column chromatography (hexane:ethyl acetate=1:2), to give 35 mg (yield: 34%) of the target compound.

1H NMR (200 MHz, CDCl$_3$) δ 1.43(s, 3H), 2.02(s, 3H), 2.07(s, 3H), 3.48(s, 3H), 3.54(s, 3H), 4.59(s, 1H), 5.63(d,

1H), 6.14(d, 1H), 6.57(d, 1H), 6.67(d, 1H), 6.94-6.98(m, 2H), 7.08-7.15(m, 2H), 7.62(dd, 1H), 11.85(br-s, 1H)

Example 15

Preparation of (2S, 3R, 4S)-6-benzoylamino-3,4-dihydro-3-hydroxy-2-dimethoxymethyl-2-methyl-4-(2,3-dihydro-2-cyanoimino-1H-benzimidazol-1-yl)-2H-1-benzopyran 100 mg (0.24 mmol) of the compound obtained in example 5 was dissolved in 1 ml of THF, then 28 μl (0.24 mmol) of benzoyl chloride and 51 μl (0.37 mmol) of triethylamine were added thereto. The reaction was stirred at room temperature for 2 hours, 10 ml of saturated NaHCO$_3$ solution was added, and aqueous layer was extracted with 20 ml of ethyl acetate. Organic layer was dried over anhydrous MgSO$_4$, and concentrated under reduced pressure. The residue was purified by silica gel column chromatography (hexane:ethyl acetate=1:2), to give 68 mg (yield: 54%) of the target compound.

$^1$H NMR (200 MHz, CDCl$_3$) δ 1.60(s, 3H), 3.55(s, 6H), 4.25(dd, 1H), 4.61(s, 1H), 5.95(d, 1H), 6.44(d, 1H), 6.87-6.94(m, 2H), 7.00(d, 1H), 7.08(dd, 1H), 7.37-7.48(m, 3H), 7.77(m, 3H), 7.85(dd, 1H)

Example 16

Preparation of (2S, 3R, 4S)-6-(trifluoroacetyl)amino-3,4-dihydro-3-hydroxy-2-dimethoxymethyl-2-methyl-4-(2,3-dihydro-2-cyanoimino-1H-benzimidazol-1-yl)-2H-1-benzopyran Reaction of 120 mg (0.29 mmol) of the compound prepared in the example 5 with 41 μl (0.29 mmol) of trifluoroacetic anhydride was performed in analogy to the procedure described example 11 to give 30 mg (yield: 21%) of the target compound.

$^1$H NMR (200 MHz, CDCl$_3$) δ 1.61(s, 3H), 3.53(s, 3H), 3.55(s, 3H), 4.23(m, 1H), 4.57(s, 1H), 5.98(d, 1H), 6.39(d, 1H), 6.86-7.14(m, 4H), 7.73(dd, 1H), 8.06(s, 1H)

Example 17

Preparation of (2S, 3R, 4S)-6-methanesulfonylamino-3,4-dihydro-3-hydroxy-2-dimethoxymethyl-2-methyl-4-(2,3-dihydro-2-cyanoimino-1H-benzimidazol-1-yl)-2H-1-benzopyran 120 mg (0.29 mmol) of the compound obtained in example 5 was dissolved in 2 ml of methylenechloride, then 23 μl (0.29 mmol) of methanesulfonyl chloride and 76 μl (0.44 mmol) of diisopropylethylamine were added thereto. The reaction was stirred at room temperature for 14 hours, saturated NaHCO$_3$ solution was added, and aqueous layer was extracted with 30 ml of methylenechloride. Organic layer was dried over anhydrous MgSO$_4$, concentrated under reduced pressure. The residue was purified by silica gel column chromatography (hexane:ethyl acetate=1:1), to give 35 mg (yield: 26%) of the target compound.

$^1$H NMR (200 MHz, CDCl$_3$) δ 1.60(s, 3H), 2.62(s, 3H), 3.55(s, 6H), 4.20(dd, 1H), 4.59(s, 1H), 5.96(d, 1H), 6.33(d, 1H), 6.67(d, 1H), 6.81-6.98(m, 3H), 7.08(dd, 1H), 7.31(m, 1H)

Example 18

Preparation of (2S, 3R, 4S)-6-nitro-3,4-dihydro-3-hydroxy-2-dimethoxymethyl-2-methyl-4-(2,3-dihydro-2-oxo-1H-benzimidazol-1-yl)-2H-1-benzopyran 391 mg (1.0 mmol) of the compound obtained in the step 1 of the example 1 was dissolved in 4 ml of methylenechloride, then 262 mg (1.21 mmol) of di-2-pyridyl carbonate and 12 mg (0.10 mmol) of 4-dimethylaminopyridine were added thereto. The reaction was stirred at room temperature for 1 hour, solvent was evaporated under reduced pressure. The residue was purified by silica gel column chromatography, to give 193 mg (yield: 47%) of the target compound.

$^1$H NMR (200 MHz, CDCl$_3$) δ 1.26(s, 3H), 3.47(s, 3H), 3.53(s, 3H), 4.23(br, 2H), 4.57(s, 1H), 5.96(d, 1H), 6.01(d, 1H), 6.80(t, 1H), 6.99-7.26(m, 4H), 7.89(s, 1H), 8.10(dd, 1H), 8.91(s, 1H) Mass: 415, 324, 206, 190

Example 19

Preparation of (2S, 3R, 4S)-6-amino-3,4-dihydro-3-hydroxy-2-dimethoxymethyl-2-methyl-4-(2,3-dihydro-2-oxo-1H-benzimidazol-1-yl)-2H-1-benzopyran Reaction of 100 mg (0.24 mmol) of the compound prepared in example 18 was performed in analogy to the procedure described in the example 5, to give 58 mg (yield: 63%) of the target compound.

$^1$H NMR (200 MHz, CDCl$_3$) δ 1.54(s, 3H), 3.36(br, NH2), 3.52(s, 6H), 4.19(t, 1H), 4.61(s, 1H), 5.67(d, 1H), 6.33(m, 2H), 6.57(m, 1H), 6.77(m, 2H), 6.95(m, 2H), 9.73(s, NH) Mass: 385(M+), 292, 176, 160

Example 20

Preparation of (3R, 4S)-6-nitro-3,4-dihydro-3-hydroxy-2,2-dimethyl-4-(2,3-dihydro-2-oxo-1H-benzimidazol-1-yl)-2H-1-benzopyran <Step 1> Preparation of (3R, 4S)-6-nitro-3,4-dihydro-3-hydroxy-2,2-dimethyl-4-[(2-aminophenyl)amino]-2H-1-benzopyran Reaction of 1.0 g (4.53 mmol) of epoxide compound (3R, 4R)-6-nitro-3,4-dihydro-3,4-epoxy-2,2-dimethyl-2H-1-benzopyran with 0.49 g (4.53 mmol) of 1,2-phenylinediamine was performed in analogy to the procedure described in the step 1 of the example 1, to give 0.51 g (yield: 32%) of the target compound.

$^1$H NMR (200 MHz, CDCl$_3$) δ 1.34(s, 3H), 1.53(s, 3H), 3.75(d, 1H), 4.51(d, 1H), 6.70(m, 5H), 8.01(dd, 1H), 8.28(s, 1H)

<Step 2> Preparation of (3R, 4S)-6-nitro-3,4-dihydro-3-hydroxy-2,2-dimethyl-4-(2,3-dihydro-2-oxo-1H-benzimidazol-1-yl)-2H-1-benzopyran Reaction of 504 mg (1.80 mmol) of the compound prepared in the above step 1 was performed in analogy to the procedure described in the example 18, to give 410 mg (yield: 65%) of the target compound.

$^1$H NMR (200 MHz, CDCl$_3$) δ 1.42(s,3H), 1.62(s,3H), 3.59(br-s, 1H—OH), 4.18(m,1H), 5.67(d,1H), 6.15(d,1H), 6.77(t,1H), 6.93(m,3H), 7.82(s,1H), 8.10(dd,1H), (br-s, 1H)

Example 21

Preparation of (3R, 4S)-6-amino-3,4-dihydro-3-hydroxy-2,2-dimethyl-4-(2,3-dihydro-2-oxo-1H-benzimidazol-1-yl)-2H-1-benzopyran Reaction of 130 mg (0.37 mmol) of the compound prepared in example 20 was performed in analogy to the procedure described in the example 5, to give 110 mg (yield: 92%) of the target compound.

$^1$H NMR (200 MHz, CDCl$_3$) δ 1.37(s, 3H), 1.50(s, 3H), 3.37(br-s, 2H, —NH2), 4.07(br-s, 1H, —OH), 5.39(d, 1H), 6.31(dd, 1H), 6.62(dd, 1H), 6.74(d, 1H), 6.91(m, 2H), 7.20(d, 2H)

Example 22

Preparation of (2S, 3R, 4S)-6-nitro-3,4-dihydro-3-hydroxy-2-dimethoxymethyl-2-methyl-4-(2,3-dihydro-2-thioxo-1H-benzimidazol-1-yl)-2H-1-benzopyran Reaction of 300 mg (0.77 mmol) of the compound prepared in the step 1 of the example 1 with 197 mg (0.85 mmol) of di-2-pyridyl thiocarbonate and 9 mg (0.08 mmol) of 4-dimethylaminopyridine was performed in analogy to the procedure described in the example 18, to give 240 mg (yield: 77%) of the target compound.

$^1$H NMR (300 MHz, CDCl$_3$+1 drop DMSO) δ 1.65(s, 3H), 3.57(s, 3H), 3.60(s, 3H), 4.34(t, 1H), 4.69(s, 1H), 6.35(d, 1H), 6.90-7.15(m, 4H), 7.27(m, 2H), 7.71(s, 1H), 8.13(dd, 1H), 11.7(br, 1H) Mass: 431(M+), 353, 338, 206, 190

Example 23

Preparation of (3R, 4S)-6-nitro-3,4-dihydro-3-hydroxy-2,2-dimethyl-4-(2,3-dihydro-2-thioxo-1H-benzimidazol-1-yl)-2H-1-benzopyran Reaction of 400 mg (1.21 mmol) of the compound prepared in the step 1 of the example 20 with 280 mg (1.21 mmol) of di-2-pyridyl thiocarbonate was performed in analogy to the procedure described in the example 22, to give 250 mg (yield: 56%) of the target compound.

$^1$H NMR (200 MHz, CDCl$_3$) δ 1.48(s, 3H), 1.60(s, 3H), 3.17(br-s, 1H, OH), 4.26(m, 1H), 6.28(d, 1H), 6.80(d, 1H), 6.96(m, 4H), 7.71(s, 1H), 8.11(dd, 1H), 10.32(s, 1H, NH)

Example 24

Preparation of (3R, 4S)-6-amino-3,4-dihydro-3-hydroxy-2,2-dimethyl-4-(2,3-dihydro-2-thioxo-1H-benzimidazol-1-yl)-2H-1-benzopyran Reaction 145 mg (0.39 mmol) of the compound prepared in the example 23 was performed in analogy to the procedure described in the example 5, to give 115 mg (yield: 86%) of the target compound.

$^1$H NMR (200 MHz, CDCl$_3$) δ 1.24(s, 3H), 1.39(s, 3H), 3.98(m, 2H), 4.48(br-s, 1H), 5.26(d, 1H), 5.50(d, 1H), 5.71(s, 2H), 6.02(s, 1H), 6.32(m, 1H), 6.77(m, 2H), 10.90(s, 1H) Mass: 341, 320, 204, 106

Example 25

Preparation of (2S, 3R, 4S)-6-nitro-3,4-dihydro-3-hydroxy-2-diethoxymethyl-2-methyl-4-(2,3-dihydro-2-cyanoimino-1H-benzimidazol-1-yl)-2H-1-benzopyran <Step 1> Preparation of (2S, 3R, 4S)-6-nitro-3,4-dihydro-3-hydroxy-2-diethoxymethyl-2-methyl-4-[(2-aminophenyl)amino]-2H-1-benzopyran Reaction of 708 mg (2.29 mmol) of epoxide compound (2S, 3R, 4R)-6-nitro-3,4-dihydro-3,4-epoxy-2-diethoxy-2-methyl-2H-1-benzopyran with 495 mg (4.58 mmol) of 1,2-phenylinediamine was performed in analogy to the procedure described in the example 1, to give 791 mg (yield: 83%) of the target compound.

$^1$H NMR (200 MHz, CDCl$_3$) δ 1.12(t, 3H), 1.20(t, 3H), 1.51(s, 3H), 3.62(m, 2H), 3.65(br-s, 2H, NH2), 3.81(m, 2H), 3.92(d, 1H), 4.08(m, 2H, NH, OH), 4.62(s, 1H), 4.69(dd, 1H), 6.74-6.90(m, 4H), 6.93(d, 1H), 8.08(dd, 1H), 8.34(d, 1H)

<Step 2> Preparation of (2S, 3R, 4S)-6-nitro-3,4-dihydro-3-hydroxy-2-diethoxymethyl-2-methyl-4-(2,3-dihydro-2-cyanoimino-1H-benzimidazol-1-yl)-2H-1-benzopyran Reaction of 200 mg (0.48 mmol) of the compound prepared in the above step 1 was performed in analogy to the procedure described in the step 2 of the example 1, to give 51 mg (yield: 23%) of the target compound.

$^1$H NMR (300 MHz, CDCl$_3$) δ 1.12(t, 3H), 1.29(t, 3H), 1.63(s, 3H), 3.59(m, 2H), 3.67(d, 1H), 3.83(m, 2H), 4.22(dd, 1H), 4.72(s, 1H), 6.18(d, 1H), 6.28(d, 1H), 6.92(dd, 1H), 7.04(d, 1H), 7.13(dd, 1H), 7.36(d, 1H), 7.78(d, 1H), 8.15(dd, 1H)

Example 26

Preparation of (2S, 3R, 4S)-6-nitro-3,4-dihydro-3-hydroxy-2-methoxymethyl-2-methyl-4-(2,3-dihydro-2-cyanoimino-1H-benzimidazol-1-yl)-2H-1-benzopyran <Step 1> Preparation of (2S, 3R, 4S)-6-nitro-3,4-dihydro-3-hydroxy-2-methoxymethyl-2-methyl-4-[(2-aminophenyl)amino]-2H-1-benzopyran Reaction of 300 mg (1.19 mmol) of epoxide compound (2S, 3R, 4R)-6-nitro-3,4-dihydro-3,4-epoxy-2-methoxymethyl-2-methyl-2H-1-benzopyran with 258 mg (2.39 mmol) of 1,2-phenylinediamine was performed in analogy to the procedure described in the step 1 of the example 1, to give 364 mg (yield: 85%) of the target compound.

$^1$H NMR (300 MHz, CDCl$_3$) δ 1.48(s, 3H), 3.38(s, 3H), 3.69(dd, 2H), 3.95(d, 1H), 4.72(d, 1H), 6.71-6.88(m, 4H), 6.95(d, 1H), 8.07(dd, 1H), 8.29(d, 1H) Mass: 359, 296, 256, 119, 107, 80

<Step 2> Preparation of (2S, 3R, 4S)-6-nitro-3,4-dihydro-3-hydroxy-2-methoxymethyl-2-methyl-4-(2,3-dihydro-2-cyanoimino-1H-benzimidazol-1-yl)-2H-1-benzopyran Reaction of 279 mg (0.78 mmol) of the compound prepared in the above step 1 was performed in analogy to the procedure described in the step 2 of the example 1, to give 183 mg (yield: 58%) of the target compound.

$^1$H NMR (300 MHz, CDCl$_3$) δ 1.65(s, 3H), 3.41(s, 3H), 3.76(dd, 2H), 4.26(d, 1H), 6.10(d, 1H), 6.30(d, 1H), 6.89(d, 1H), 7.03(d, 1H), 7.27(m, 2H), 7.73(d, 1H), 8.14(dd, 1H), 11.88(br-s, 1H) Mass: 409, 346, 206, 158, 132, 57

Example 27

Preparation of (2S, 3R, 4S)-6-amino-3,4-dihydro-3-hydroxy-2-methoxymethyl-2-methyl-4-(2,3-dihydro-2-cyanoimino-1H-benzimidazol-1-yl)-2H-1-benzopyran Reaction of 141 mg (0.35 mmol) of the compound prepared in example 26 was performed in analogy to the procedure described in the example 5, to give 38 mg (yield: 29%) of the target compound.

$^1$H NMR (300 MHz, CDCl$_3$) δ 1.65(s, 3H), 3.34(br-s, 1H), 3.44(s, 3H), 3.56(d, 1H), 3.89(d, 1H), 4.23(d, 1H), 5.84(d, 1H), 6.19(d, 1H), 6.49(d, 1H), 6.60(dd, 1H), 6.77(d, 1H), 6.93(t, 1H), 7.09(t, 1H), 7.30(d, 1H) Mass: 379, 319, 287, 133, 121

Example 28

Preparation of (2S, 3R, 4S)-6-nitro-3,4-dihydro-3-hydroxy-2-methoxymethyl-2-methyl-4-(2,3-dihydro-2-cyanoimino-1H-6-methylbenzimidazol-1-yl)-2H-1-benzopyran <Step 1> Preparation of (2S, 3R, 4S)-6-nitro-3,4-dihydro-3-hydroxy-2-methoxymethyl-2-methyl-4-[(2-amino-5-methylphenyl)amino]-2H-1-benzopyran Reaction of 300 mg (1.19 mmol) of epoxide compound (2S, 3R, 4R)-6-nitro-3,4-dihydro-3,4-epoxy-2-methoxymethyl-2-methyl-2H-1-benzopyran with 146 mg (1.19 mmol) of 3,4-diaminotoluene was performed in analogy to the procedure described in 44%) of the target compound.

$^1$H NMR (300 MHz, CDCl$_3$) δ 1.46(s, 3H), 2.26(s, 3H), 3.36(s, 3H), 3.66(m,3H), 3.37(d, 1H), 4.66(t, 1H), 6.52-6.73 (m, 3H), 6.95(dd, 1H), 8.04(dd, 1H), 8.30(dd, 1H) Mass: 373, 310, 146, 133, 121, 83

<Step 2> Preparation of (2S, 3R, 4S)-6-nitro-3,4-dihydro-3-hydroxy-2-methoxymethyl-2-methyl-4-(2,3-dihydro-2-cyanoimino-1H-6-methylbenzimidazol-1-yl)-2H-1-benzopyran Reaction of 144 mg (0.39 mmol) of the compound prepared in the above step 1 was performed in analogy to the procedure described in the step 2 of the example 1, to give 54 mg (yield: 33%) of the target compound.

$^1$H NMR (300 MHz, CDCl$_3$) δ 1.65(s, 3H), 3.27(s, 3H), 3.41(s, 3H), 3.77(dd, 2H), 4.26(dd, 1H), 6.60(dd, 1H), 6.16(d, 1H), 7.06(m, 2H), 7.16(d, 1H), 7.73(d, 1H), 8.13(dd, 1H) Mass: 423, 380, 335, 289, 172, 147, 57

Example 29

Preparation of (2S, 3R, 4S)-6-nitro-3,4-dihydro-3-hydroxy-2-([1,3]dioxan-2-yl)-2-methyl-4-(2,3-dihydro-2-cyanoimino-1H-benzimidazol-1-yl)-2H-1-benzopyran <Step 1> Preparation of (2S, 3R, 4S)-6-nitro-3,4-dihydro-3-hydroxy-2-([1,3]dioxan-2-yl)-2-methyl-4-[(2-aminophenyl)amino]-2H-1-benzopyran Reaction of 400 mg (1.36 mmol) of epoxide compound (2S, 3R, 4R)-6-nitro-3,4-dihydro-3,4-epoxy-2-([1,3]dioxan-2-yl)-2-methyl-2H-1-benzopyran with 295 mg (2.73 mmol) of 1,2-phenylenediamine was performed in analogy to the procedure described in the step 1 of the example 1, to give 500 mg (yield: 92%) of the target compound.

$^1$H NMR (300 MHz, CDCl$_3$) δ 1.41(d, 1H), 1.50(s, 3H), 2.14(m, 1H), 3.35(br-s, 2H), 3.81(m, 2H), 3.87(br-s, 1H), 4.11(m, 1H), 4.19(m, 2H), 4.69(d, 1H), 4.85(s, 1H), 6.71-6.88(m, 4H), 7.00(d, 1H), 8.07(dd, 1H), 8.32(d, 1H)

<Step 2> Preparation of (2S, 3R, 4S)-6-nitro-3,4-dihydro-3-hydroxy-2-([1,3]dioxan-2-yl)-2-methyl-4-(2,3-dihydro-2-cyanoimino-1H-benzimidazol-1-yl)-2H-1-benzopyran Reaction of 400 mg (1.0 mmol) of the compound prepared in the above step 1 was performed in analogy to the procedure described in the step 2 of the example 1, to give 269 mg (yield: 60%) of the target compound.

1H NMR (300 MHz, CDCl$_3$) δ 1.46(d, 1H), 1.70(s, 3H), 2.22(m, 1H), 3.81(m, 2H), 4.25(m, 3H), 4.94(s, 1H), 6.27(d, 1H), 6.31(d, 1H), 6.91(dd, 1H), 7.06(d, 1H), 7.11(dd, 1H), 7.28(d, 1H), 7.75(d, 1H), 8.13(dd, 1H)

Example 30

Preparation of (2S, 3R, 4S)-6-amino-3,4-dihydro-3-hydroxy-2-([1,3]dioxan-2-yl)-2-methyl-4-(2,3-dihydro-2-cyanoimino-1H-benzimidazol-1-yl)-2H-1-benzopyran Reaction of 173 mg (0.38 mmol) of the compound prepared in example 29 was performed in analogy to the procedure described in the example 12, to give 25 mg (yield: 15%) of the target compound.

$^1$H NMR (300 MHz, CDCl$_3$) δ 1.42(d, 1H), 1.71(s, 3H), 2.18(m, 1H), 3.50(d, 2H), 3.75(dd, 1H), 3.92)dd, 1H), 4.18-4.31(m, 3H), 5.00(s, 1H), 5.90(d, 1H), 6.18(d, 1H), 6.47(d, 1H), 6.60(dd, 1H), 6.83(d, 1H), 6.92(dd, 1H), 7.08 (dd, 1H), 7.23(d, 1H), 11.86(br-s, 1H) Mass: 421(M$^+$)

Example 31

Preparation of (2S, 3R, 4S)-6-nitro-3,4-dihydro-3-hydroxy-2-([1,3]dioxolan-2-yl)-2-methyl-4-(2,3-dihydro-2-cyanoimino-1H-benzimidazol-1-yl)-2H-1-benzopyran <Step 1> Preparation of (2S, 3R, 4S)-6-nitro-3,4-dihydro-3-hydroxy-2-([1,3]dioxolan-2-yl)-2-methyl-4-[(2-aminophenyl)amino]-2H-1-benzopyran Reaction of 417 mg (1.49 mmol) of epoxide compound (2S, 3R, 4R)-6-nitro-3,4-dihydro-3,4-epoxy-2-([1,3]dioxolan-2-yl)-2-methyl-2H-1-benzopyran with 323 mg (3.00 mmol) of 1,2-phenylinediamine was performed in analogy to the procedure described in the step 1 of the example 1, to give 596 mg (yield: 87%) of the target compound.

1H NMR (300 MHz, CDCl$_3$) δ 1.54(s, 3H), 3.40(br-s, 3H), 3.80-4.08(m, 6H), 4.11(m, 1H), 4.86(d, 1H), 5.26(s, 1H), 6.75-6.87(m, 4H), 6.95(d, 1H), 8.06(dd, 1H), 8.27(d, 1H)

<Step 2> Preparation of (2S, 3R, 4S)-6-nitro-3,4-dihydro-3-hydroxy-2-([1,3]dioxolan-2-yl)-2-methyl-4-(2,3-dihydro-2-cyanoimino-1H-benzimidazol-1-yl)-2H-1-benzopyran Reaction of 200 mg (0.52 mmol) of the compound prepared in the above step 1 was performed in analogy to the procedure described in the step 2 of the example 1, to give 140 mg (yield: 62%) of the target compound.

$^1$H NMR (300 MHz, CDCl$_3$) δ 1.59(s, 3H), 3.53(m, 1H), 3.80(m, 1H), 3.88(m, 1H), 3.98(m, 1H), 4.40(d, 1H), 5.39(s, 1H), 6.24(d, 1H), 6.53(d, 1H), 7.00(dd, 1H), 7.08(d, 1H), 7.18(dd, 1H), 7.33(dd. 1H), 7.55(d, 1H), 8.10(dd, 1H) Mass: 437(M$^+$)

Example 32

Preparation of (2S, 3R, 4S)-6-nitro-3,4-dihydro-3-hydroxy-2-([1,3]-5,5-dimethyldioxan-2-yl)-2-methyl-4-(2,3-dihydro-2-cyanoimino-1H-benzimidazol-1-yl)-2H-1-benzopyran <Step 1> Preparation of (2S, 3R, 4S)-6-nitro-3,4-dihydro-3-hydroxy-2-([1,3]-5,5-dimethyldioxan-2-yl)-2-methyl-4-[(2-aminophenyl)amino]-2H-1-benzopyran Reaction of 400 mg (1.24 mmol) of epoxide compound (2S, 3R, 4R)-6-nitro-3,4-dihydro-3,4-epoxy-2-([1,3]-5,5-dimethyldioxan-2-yl)-2-methyl-2H-1-benzopyran with 269 mg (2.49 mmol) of 1,2-phenylenediamine was performed in analogy to the procedure described in the step 1 of the example 1, to give 474 mg (yield: 89%) of the target compound.

$^1$H NMR (300 MHz, CDCl$_3$) δ 0.75(s, 3H), 1.19(s, 3H), 1.54(s, 3H), 3.36(br-s, 2H), 3.48(m, 2H), 3.71(m, 2H), 3.78(br-s, 1H), 3.91(br-s, 1H), 4.14(d, 1H), 4.70(br-s, 1H), 4.75(s, 1H), 6.71-6.88(m, 4H), 7.00(d, 1H), 8.08(dd, 1H), 8.33(d, 1H)

<Step 2> Preparation of (2S, 3R, 4S)-6-nitro-3,4-dihydro-3-hydroxy-2-([1,3]-5,5-dimethyldioxan-2-yl)-2-methyl-4-(2,3-(2,3-dihydro-2-cyanoimino-1H-benzimidazol-1-yl)-2H-1-benzopyran Reaction of 200 mg (0.47 mmol) of the compound prepared in the above step 1 was performed in analogy to the procedure described in the step 2 of the example 1, to give 178 mg (yield: 79%) of the target compound.

$^1$H NMR (300 MHz, CDCl$_3$) δ 0.77(s, 3H), 1.33(s, 3H), 1.72(s, 3H), 3.46(d, 1H), 3.52(d, 1H), 3.64(br-s, 1H), 3.76(d, 2H), 4.26(d, 1H), 4.83(s, 1H), 6.28(d, 1H), 6.31(d, 1H), 6.91(dd, 1H), 7.10(m, 2H), 7.34(d, 1H), 7.76(d, 1H), 8.13(dd, 1H) Mass: 479(M$^+$)

The following experiments were performed to investigate pharmacological activities of compounds of the present invention represented in <Formula 1>.

Experiment 1: Vasodilating Effect on Blood Vessel Isolated from White Rats

In order to investigate vasorelaxation effect of compounds represented in <Formula 1> on blood vessel, following experiments were performed.

White rats (350~450 g; the Experimental Animal Team of the Korea Research Institute of Chemical Technology) were knocked to be unconscious by hitting the occipital region, sacrificed by cervical dislocation, and underwent thoracotomy. After being quickly removed, the thoracic aorta was deprived of the adipose tissue and cut into aortic rings of 3 mm width. The aorta was lightly rubbed with cotton club soaked in a modified Krebs Henseleit buffer (physiological salt solution) to remove the inner epithelial layer therefrom. While being hung in an organ bath containing a physiological buffer, the vascular smooth muscle was allowed to equilibrate under a resting tension of 2 g and then, stand for 1 hour at 37° C. for stabilization, supplying a carbogen consisting of 95% O$_2$/5% CO$_2$. Thereafter, the vascular smooth muscle was constricted with 10$^{-5}$ M phenylephrine and washed several times with physiological saline solution. The said procedure was repeated to ensure the stable reactivity of vascular smooth muscle to repetitive constriction/relaxation.

Thereafter, 3×10$^{-6}$ M methoxamine was applied to induce an intensive constriction in the vascular smooth muscle. When the vasoconstriction induced by the methoxamine was reached and maintained to a maximum, test compounds and control material were cumulatively added to the organ bath with concentration of 1, 3, 10 and 30 μM, respectively, to examine the vasodilating effect. Cromakalim and BMS-180448 (compound of <Formula 2>), known to be the first generation K$_{ATP}$ opener with potent vasodilating effect, were used as control materials.

The change rate of constriction by the addition of the drugs compared to the maximal constriction induced by methoxamine was calculated to plot a concentration-relaxation response curve. Through a least linear regression analysis, IC$_{50}$ that the drug concentration at which the vascular tissue is relaxed to 50% extent of the maximal constriction, was obtained for each drug. And the results were shown in the below Table 1.

TABLE 1

Vasodilating effect of the compounds of <Formula 1>

| Compound | Concentration for inhibition of constriction induced by methoxamine in rat arota (IC$_{50}$, μM) |
|---|---|
| Cromakalim | 0.067 |
| BMS-180448 | 1.38 |
| Compound of Example 1 | 50.1 |
| Compound of Example 20 | 18.6 |

As shown in the above Table 1, Cromakalim represented a potent vasorelaxation effect, showing 0.067 μM of IC$_{50}$ on the isolated rat aorta constricted with methoxamine (3 μM) while IC$_{50}$ of BMS-180448 was 1.38 μM, which was twenty times weaker vasorelaxation effects than that of Cromakalim. On the other hand, IC$_{50}$ of the compound of example 1 was 50.1 μM, showing 36 times weaker vasorelaxation effect than that of BMS-180448, a general K$_{ATP}$ opener, used as a control material. The compound of example 20 also showed 10 times weaker vasorelaxation effect than that of BMS-180448.

Cromakalim or BMS-180448 protects heart by acting toward K$_{ATP}$ in heart and drops blood pressure by dilating blood vessels by acting toward K$_{ATP}$ in coronary and peripheral blood vessels. Hypotensive action may mask any cardioprotective effects due to reduction under coronary artery perfusion pressure, and would limit utility in treating myocardial ischemia. Therefore, the compounds of the present invention may be more optimal for cardioprotective agents by virtue of their weak vasorelaxation activity.

Again, the compounds of the present invention have enhanced cardioprotective function with weak vasorelaxation effect.

Experiment 2: Cardioprotective Effect on Isolated Ischemic Heart Models of White Rats The experiment confirming that the compounds of <Formula 1> have the protective effect (antiischemic effect) on ischemic heart was accomplished in the below.

100 mg/kg of sodium pentobarbital was injected in abdominal cavity of white male rats (300~450 g; the experimental animal team of the Korea Research Institute of Chemical Technology) to anesthetize them. Then, an intravenous injection of 1000 U/kg of heparin was performed before taking out heart. Particularly, cannula(PE 240) was inserted in the trachea, and artificial respiration was tried upon the rat by using a rodent ventilator. Under that condition, aortic cannula was inserted in the aorta and heart was taken out under retrograde perfusion. The extracted heart was hung on Langendorff apparatus quickly and unnecessary tissues on heart were removed. Perfusion was induced under static pressure (85 mmHg) with 37° C. modified Krebs-Henseleit bicarbonate buffer (composition <mM/L>: 116 NaCl, 4.7 KCl, 1.1 $MgSO_4$, 1.17 $KH_2PO_4$, 24.9 $NaHCO_3$, 2.52 $CaCl_2$, 8.32 Glucose, 2.0 Pyruvate) saturated with 95% $O_2$/5% $CO_2$. A metal cannula, to which a latex balloon filled with a ethanol-distilled water mixture (1:1 vol/vol) was linked, was inserted in left ventricle through pulmonary vein. Then, left ventricular pressure transmitted through the balloon was transduced by using pressure transducer, and amplified by using isovolumetric amplifier(Plugsys bridge amplifier). Then, the pressure was recorded in a recorder (Linearcorder mark 8 WR 3500). Thereafter, heart was stabilized for 15 minutes. Then, left ventricular end diastolic pressure (LVEDP) was given by 5 mmHg and such volume of the balloon was kept throughout the experiments.

Baseline cardiac contractile function, heart rate (HR), and coronary flow (CF) were measured. Cardiac contractile function was calculated by subtracting LVSP (left ventricular peak systolic pressure) from LVEDP (left ventricular end diastolic pressure), yielding LVDP (left ventricular developed pressure). Double product RPP (rate-pressure product) (DP), another important parameter for indirectly assessing cardiac performance in Langendorff heart, in which cardiac output could not be measured ordinarily, was calculated by multiplying HR by LVDP. Throughout the experiment, total coronary blood flow was measured by the use of coronary flow probe (diameter: 1.0 mm) installed in aortic cannula with electromagnetic flowmeter. Temperature of heart was steadily maintained by immersing the heart at 37° C. in physiological saline solution to which 95% $O_2$/5% $CO_2$ was constantly supplied. After stabilization for 15 min, the hearts were pre-treated for 10 min with vehicle (0.04% DMSO) only or a compound of the present invention or the control material in the vehicle. Thereafter, cardiac contractile function, HR and CF were repeatedly measured. Global ischemia was induced by completely shutting off the perfusate for 30 min. Severity of ischemia was determined as the time to contracture (TTC, min) during global ischemia in which the first 5 mmHg increase in EDP was observed. Then, the hearts were reperfused and, 30 min later, contractile functions (LVDP, HR and CF) were repeatedly measured. After reperfusion was accomplished for 30 min, LDH (lactate dehydrogenase) was measured with a kit as a sensitive index for loss of cell viability. The results were shown in Table 2.

TABLE 2

Cardioprotective effect in ischemic heart models of rats

| Compound | LVDP × HR[1] (%) | EDP[2] (mmHg) | TTC[3] (minute) | LDH[4] (unit/g) |
|---|---|---|---|---|
| Vehicle | 15.8 | 45.1 | 19.8 | 31.3 |
| BMS-180448 | 67.6 | 16.5 | 27.8 | 17.2 |
| Compound of Example 1 | 68.8 | 20.3 | 23.2 | 8.1 |
| Compound of Example 18 | 41.5 | 29.3 | 24.2 | 20.4 |
| Compound of Example 20 | 55.5 | 29.0 | 23.9 | 20.7 |

[1]left ventricular developed pressure × heart rate
[2]left ventricular end diastolic pressure
[3]time to induce contraction
[4]concentration of lactate dehydrogenase In vehicle-treated group, reperfusion DP (LVDP×HR), an index for contractility function, was decreased to 15.8% of pre-treatment DP, and EDP was increased to 45.1 mmHg from 5 mmHg, and TTC was 19.8 min, and reperfusion LDH release was 31.3 unit/g as shown in the above.

In BMS-180448 treated group, reperfusion contractile function (DP, LVDP×HR) was 67.6% of pre-treatment DP, which was significantly improved compared to the vehicle treated group. EDP was 16.5 mmHg, significantly lower than control, and TTC was 27.8 min, prolonged than control, and reperfusion LDH release was 17.2 Unit/g, decreased than control. Then, in BMS-180448 treated group, all parameters showed significant protective effect on ischemic heart.

When compared only in antiischemic effects based on those parameters, cardiac contractile function, EDP, TTC, and LDH release, the compounds of the present invention were similar to or superior to BMS-180448. However, because the compounds of the present invention have remarkably lower vasorelaxant effects than BMS-180448 dose, they are far superior to the conventional drugs in cardioselective antiischemic activity. Especially, the compound of Example 1 showed a good cardioprotective effect, of which contractile function (LVDP×HR) was improved to 68.8% of pre-treatment index, and EDP was 20.3 mmHg, and TTC was 23.2 min, and reperfusion LDH release was 8.1 unit/g, with very low vasodilation activity ($IC_{50}$=50.1 μM). So, it shows much better cardioselectivity upon vasodilation than BMS-180448. Consequently, the compounds of the present invention can be used for the treatment of ischemic heart diseases by virtue of their excellent selectivity and protective activity against ischemic cardiovascular diseases. Besides, the compounds can also be used as a protective agent for ischemic brain and retinal cell damage caused by ischemia-reperfusion or for storage organs.

Experimental 3: Acute Oral Toxicity Test in Rats

The following experiments were performed to see if the compounds of <Formula 1> had acute toxicity in rats.

6-week old SPF SD line rats were used in the tests for acute toxicity test. The compounds prepared in the Example 1 were suspended in 0.5% methylcellulose solution and orally administered once to 2 rats per group with the dosage of 1 g/kg/15 ml. Death, clinical symptoms, and weight change in rats were observed, hematological tests and biochemical tests of blood were performed, and any abnormal signs in the gastrointestinal organs of chest and abdomen were checked with eyes during autopsy.

The results showed that the test compounds did not cause any specific clinical symptoms, weight change, or death in rats. No change was observed in hematological tests, biochemical tests of blood, and autopsy. The compounds used in this experiment were evaluated to be safe substances since they did not cause any toxic change in rats up to the level of 2 g/kg and their estimated $LD_{50}$ values were much greater than 2 g/kg in rats.

INDUSTRIAL APPLICABILITY

As explained hereinbefore, the compounds of present invention represented in <Formula 1> have excellent cardioprotective effect against damage by ischemia-reperfusion without lowering blood pressure owing to their weak vasorelaxation activity. Thus, a pharmaceutical composition containing benzopyran derivatives substituted with a benzimidazole derivative, represented in <Formula 1>, or pharmaceutically acceptable salts of the same can be used as a protective or therapeutic agent for ischemia-reperfusion related damage or diseases, that is, the compounds are not only useful for the treatment of ischemic heart diseases such as myocardial infarction, unstable angina pectoris, etc, the protection of heart from the damage caused by thrombolytics or reperfusion therapy such as PTCA (percutaneous transluminal coronary angioplasty) and CABG (coronary artery bypass graft), and the protection of ischemia-reperfusion related tissues such as nerve cells, brain, retinal cells, storage organs, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A compound of <Formula 1>

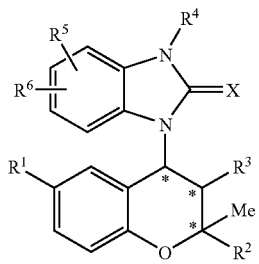

wherein
X is O, S or NCN;
R$^1$ is NO$_2$, NH$_2$, H, CN, NHCOCH$_3$, NHCOCF$_3$ or NHSO$_2$CH$_3$;
R$^2$ is

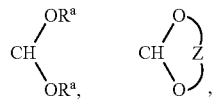

or CH$_2$OR$^a$
wherein,
R$^a$ is C$_1$~C$_4$ straight or branched alkyl; and
Z is C$_2$~C$_6$ straight or branched alkyl;
R$^3$ is OH or OCOCH$_3$;
R$^4$ is C$_1$~C$_4$ straight or branched alkyl;
R$^5$ and R$^6$ are independently H, C$_1$~C$_4$ straight or branched alkyl, alkoxy or halogen; and
* represents a chiral carbon, an enantiomer, a diastereomer, a racemic mixture or a pharmaceutically acceptable salt thereof.

2. The compound according to claim 1, selected from the group consisting of:

1) (2S, 3R, 4S)-6-nitro-3,4-dihydro-3-hydroxy-2-dimethoxymethyl-2-methyl-4-(2,3-dihydro-2-cyanoimino-1H-benzimidazol-1-yl)2H-1-benzopyran;
2) (2R, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;
3) (2S, 3S, 4R)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;
4) (2R, 3S, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran;
5) (2S, 3R, 4S)-6-amino-3,4-dihydro-3-hydroxy-2-dimethoxymethyl-2-methyl-4-(2,3-dihydro-2-cyanoimino-1H-benzimidazol-1-yl)-2H-1-benzopyran;
6) (2S, 3R, 4S)-6-nitro-3,4-dihydro-3-hydroxy-2-dimethoxymethyl-2-methyl-4-(2,3-dihydro-3-methyl-2-cyanoimino-1H-benzimidazol-1-yl)-2H-1-benzopyran;
7) (2S, 3R, 4S)-6-nitro-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran;
8) (2S, 3R, 4S)-6-amino-3,4-dihydro-3-hydroxy-2-dimethoxymethyl-2-methyl-4-(2,3-dihydro-5,6-dimethyl-2-cyanoimino-1H-benzimidazol-1-yl)-2H-1-benzopyran;
9) (2S, 3R, 4S)-6-nitro-3,4-dihydro-3-hydroxy-2-dimethoxymethyl-2-methyl-4-(2,3-dihydro-3,5,6-trimethyl-2-cyanoimino-1H-benzimidazol-1-yl)-2H-1-benzopyran; 10) (2S, 3R, 4S)-6-amino-3,4-dihydro-3-hydroxy-2-dimethoxymethyl-2-methyl-4-(2,3-dihydro-3,5,6-trimethyl-2-cyanoimino-1H-benzimidazol-1-yl)-2H-1-benzopyran;
11) (2S, 3R, 4S)-6-nitro-3,4-dihydro-3-acetoxy-2-dimethoxymethyl-2-methyl-4-(2,3-dihydro-2-cyanoimino-1H-benzimidazol-1-yl)-2H-1-benzopyran;
12) (2S, 3R, 4S)-6-amino-3,4-dihydro-3-acetoxy-2-dimethoxymethyl-2-methyl-4-(2,3-dihydro-2-cyanoimino-1H-benzimidazol-1-yl)-2H-1-benzopyran;
13) (2S, 3R, 4S)-6-acetamino-3,4-dihydro-3-hydroxy-2-dimethoxymethyl-2-methyl-4-(2,3-dihydro-2-cyanoimino-1H-benzimidazol-1-yl)-2H-1-benzopyran;
14) (2S, 3R, 4S)-6-acetamino-3,4-dihydro-3-acetoxy-2-dimethoxymethyl-2-methyl-4-(2,3-dihydro-2-cyanoimino-1H-benzimidazol-1-yl)-2H-1-benzopyran;
15) (2S, 3R, 4S)-6-benzoylamino-3,4-dihydro-3-hydroxy-2-dimethoxymethyl-2-methyl -4-(2,3-dihydro-2-cyanoimino-1H-benzimidazol-1-yl)-2H-1-benzopyran;
16) (2S, 3R, 4S)-6-(trifluoroacetyl)amino-3,4-dihydro-3-hydroxy-2-dimethoxymethyl-2-methyl-4-(2,3-dihydro-2-cyanoimino-1H-benzimidazol-1-yl)-2H-1-benzopyran;
17) (2S, 3R, 4S)-6-methanesulfonylamino-3,4-dihydro-3-hydroxy-2-dimethoxymethyl-2-methyl-4-(2,3-dihydro-2-cyanoimino-1H-benzimidazol-1-yl)-2H-1-benzopyran;
18) (2S, 3R, 4S)-6-nitro-3,4-dihydro-3-hydroxy-2-dimethoxymethyl-2-methyl-4-(2,3-dihydro-2-oxo-1H-benzimidazol-1-yl)-2H-1-benzopyran;
19) (2S, 3R, 4S)-6-amino-3,4-dihydro-3-hydroxy-2-dimethoxymethyl-2-methyl-4-(2,3-dihydro-2-oxo-1H-benzimidazol-1-yl)-2H-1-benzopyran;
22) (2S, 3R, 4S)-6-nitro-3,4-dihydro-3-hydroxy-2-dimethoxymethyl-2-methyl-4-(2,3-dihydro-2-thioxo-1H-benzimidazol-1-yl)-2H-1-benzopyran;
25) (2S, 3R, 4S)-6-nitro-3,4-dihydro-3-hydroxy-2-diethoxymethyl-2-methyl-4-(2,3-dihydro-2-cyanoimino-1H-benzimidazol-1-yl)-2H-1-benzopyran;
26) (2S, 3R, 4S)-6-nitro-3,4-dihydro-3-hydroxy-2-methoxymethyl-2-methyl-4-(2,3-dihydro-2-cyanoimino-1H-benzimidazol-1-yl)-2H-1-benzopyran;
27) (2S, 3R, 4S)-6-amino-3,4-dihydro-3-hydroxy-2-methoxymethyl-2-methyl-4-(2,3-dihydro-2-cyanoimino-1H-benzimidazol-1-yl)-2H-1-benzopyran;
28) (2S, 3R, 4S)-6-nitro-3,4-dihydro-3-hydroxy-2-methoxymethyl-2-methyl-4-(2,3-dihydro-2-cyanoimino-1H-6-methylbenzimidazol-1-yl)-2H-1-benzopyran;
29) (2S, 3R, 4S)-6-nitro-3,4-dihydro-3-hydroxy-2-([1,3]dioxan-2-yl)-2-methyl-4-(2,3-dihydro-2-cyanoimino-1H-benzimidazol-1-yl)-2H-1-benzopyran;
30) (2S, 3R, 4S)-6-amino-3,4-dihydro-3-hydroxy-2-([1,3]dioxan-2-yl)-2-methyl-4-(2,3-dihydro-2-cyanoimino-1H-benzimidazol-1-yl)-2H-1-benzopyran;
31) (2S, 3R, 4S)-6-nitro-3,4-dihydro-3-hydroxy-2-([1,3]dioxolan-2-yl)-2-4-(2,3-dihydro-2-cyanoimino-1H-benzimidazol-1-yl)-2H-1-benzopyran; and 32) (2S, 3R, 4S)-6-nitro-3,4-dihydro-3-hydroxy-2-([1,3]-5,5-dimethyldioxan-2-yl)-2-methyl-4-(2,3-dihydro-2-cyanoimino-1H-benzimidazol-1-yl)-2H-1-benzopyran, or a pharmaceutically acceptable salt thereof.

3. A cardioprotective composition comprising a compound of claim 1 as an effective ingredient.

4. The composition of claim 3, that is protective against injury caused by repurfusion in ischemic heart.

5. The compound according to claim 1 is (2S, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran.

6. The compound according to claim 1 is (2S, 3R, 4S)-6-nitro-3,4-dihydro-3-hydroxy-2-dimethoxymethyl-2-methyl-4-(2,3-dihydro-2-oxo-1H-benzimidazol-1-yl)-2H-1-benzopyran.

7. The composition of claim 4, wherein the reperfusion is provided by percutaneous transluminal coronary angioplasty or a coronary artery bypass graft.

8. A method of protecting heart from repurfusion injury in mammals, comprising administering an effective amount of a compound of claim 1 to a mammal in need thereof.

9. The method of claim 8, wherein the compound is administered in amounts up to about 2 g/kg/dose.

10. The method of claim 8, wherein the compound is administered in amounts of from about 1 g/kg/dose to about 2 g/kg/dose.

11. The method of claim 8, wherein The compound is selected from the group consisting of (2S, 3R, 4S)-6-nitro-3,4-dihydro-3-hydroxy-2-dimethoxymethyl-2-methyl-4-(2,3-dihydro-2-cyanoimino-1H-benzimidazol-1-yl)-2H-1-benzopyran, and (2S, 3R, 4S)-6-nitro-3,4-dihydro-3-hydroxy-2-dimethoxymethyl-2-methyl-4-(2,3-dihydro-2-oxo-1H-benzimidazol-1-yl)-2H-1-benzopyran.

* * * * *